(12) United States Patent
Cheng et al.

(10) Patent No.: US 12,156,792 B2
(45) Date of Patent: Dec. 3, 2024

(54) FLUID COLLECTION ASSEMBLIES INCLUDING AT LEAST ONE INFLATION DEVICE

(71) Applicant: PureWick Corporation, El Cajon, CA (US)

(72) Inventors: Jason Jishen Cheng, Covington, GA (US); Eric Rehm, Greensboro, GA (US); Nicholas Austerman, Atlanta, GA (US)

(73) Assignee: PureWick Corporation, Covington, GA (US)

( * ) Notice: Subject to any disclaimer, the term of this patent is extended or adjusted under 35 U.S.C. 154(b) by 528 days.

(21) Appl. No.: 17/447,123

(22) Filed: Sep. 8, 2021

(65) Prior Publication Data

US 2022/0071811 A1 Mar. 10, 2022

Related U.S. Application Data

(60) Provisional application No. 63/076,474, filed on Sep. 10, 2020.

(51) Int. Cl.
*A61F 13/474* (2006.01)
*A61F 13/84* (2006.01)

(52) U.S. Cl.
CPC ............ *A61F 13/474* (2013.01); *A61F 13/84* (2013.01); *A61F 2013/8494* (2013.01)

(58) Field of Classification Search
CPC .............. A61F 13/15; A61F 2013/1539; A61F 13/474; A61F 13/493; A61F 2013/8494; A61F 2002/501; A61F 13/84
See application file for complete search history.

(56) References Cited

U.S. PATENT DOCUMENTS 737,443 A 8/1903 Mooers
1,032,841 A 7/1912 Koenig
(Continued)

FOREIGN PATENT DOCUMENTS

AU 2018216821 A1 8/2018
AU 2021299304 A1 2/2023
(Continued)

OTHER PUBLICATIONS

US 9,908,683 B2, 03/2018, Sandhausen et al. (withdrawn)
(Continued)

*Primary Examiner* — Susan S Su
*Assistant Examiner* — Ted Yang
(74) *Attorney, Agent, or Firm* — Dorsey & Whitney LLP

(57) ABSTRACT

An example fluid collection assembly includes a fluid impermeable barrier having a proximal surface and a distal surface opposite the proximal surface. The proximal surface defines an opening. The fluid collection assembly also includes at least one inflation device. The inflation device includes a bladder. The bladder may be adjacent to the distal surface of the fluid impermeable barrier or between a conduit disposed in the chamber and the distal surface. The bladder is configured to switch between a first state and at least a second state. A volume of the bladder is greater when the bladder is the second state than when the bladder is in the first state. Switching the bladder between the first and second states changes a curvature of the at least a portion of the fluid collection assembly.

20 Claims, 9 Drawing Sheets

(56) References Cited

U.S. PATENT DOCUMENTS

| | | | |
|---|---|---|---|
| 1,178,644 A | 4/1916 | Johnson |
| 1,742,080 A | 12/1929 | Jones |
| 1,979,899 A | 11/1934 | Obrien et al. |
| 2,241,010 A | 5/1941 | Chipley |
| 2,262,772 A | 11/1941 | Peder |
| 2,326,881 A | 8/1943 | Packer |
| 2,379,346 A | 6/1945 | Farrell |
| 2,485,555 A | 10/1949 | Bester |
| 2,613,670 A | 10/1952 | Edward |
| 2,616,426 A | 11/1952 | Adele |
| 2,644,234 A | 7/1953 | Earl |
| 2,648,335 A | 8/1953 | Chambers |
| 2,859,786 A | 11/1958 | Tupper |
| 2,944,551 A | 7/1960 | Carl |
| 2,968,046 A | 1/1961 | Duke |
| 2,971,512 A | 2/1961 | Reinhardt |
| 3,032,038 A | 5/1962 | Swinn |
| 3,077,883 A | 2/1963 | Hill |
| 3,087,938 A | 4/1963 | Hans et al. |
| 3,169,528 A | 2/1965 | Knox et al. |
| 3,171,506 A | 3/1965 | Therkel |
| 3,194,238 A | 7/1965 | Breece |
| 3,198,994 A | 8/1965 | Hildebrandt et al. |
| 3,221,742 A | 12/1965 | Egon |
| 3,312,221 A | 4/1967 | Overment |
| 3,312,981 A | 4/1967 | Mcguire et al. |
| 3,349,768 A | 10/1967 | Keane |
| 3,362,590 A | 1/1968 | Gene |
| 3,366,116 A | 1/1968 | Huck |
| 3,398,848 A | 8/1968 | Donovan |
| 3,400,717 A | 9/1968 | Bruce et al. |
| 3,406,688 A | 10/1968 | Bruce |
| 3,424,163 A | 1/1969 | Gravdahl |
| 3,425,471 A | 2/1969 | Yates |
| 3,511,241 A | 5/1970 | Lee |
| 3,512,185 A | 5/1970 | Ellis |
| 3,520,300 A | 7/1970 | Flower |
| 3,528,423 A | 9/1970 | Lee |
| 3,613,123 A | 10/1971 | Langstrom |
| 3,648,700 A | 3/1972 | Warner |
| 3,651,810 A | 3/1972 | Ormerod |
| 3,661,155 A | 5/1972 | Lindan |
| 3,683,918 A | 8/1972 | Pizzella |
| 3,699,815 A | 10/1972 | Holbrook |
| 3,726,277 A | 4/1973 | Hirschman |
| 3,742,952 A * | 7/1973 | Magers ............ A61M 1/684 604/133 |
| 3,757,355 A | 9/1973 | Allen et al. |
| 3,788,324 A | 1/1974 | Lim |
| 3,843,016 A | 10/1974 | Bornhorst et al. |
| 3,863,638 A | 2/1975 | Rogers et al. |
| 3,863,798 A | 2/1975 | Kurihara et al. |
| 3,864,759 A | 2/1975 | Horiuchi |
| 3,881,486 A | 5/1975 | Fenton |
| 3,881,489 A | 5/1975 | Hartwell |
| 3,915,189 A | 10/1975 | Holbrook et al. |
| 3,998,228 A | 12/1976 | Poidomani |
| 3,999,550 A | 12/1976 | Martin |
| 4,015,604 A | 4/1977 | Csillag |
| 4,020,843 A | 5/1977 | Kanall |
| 4,022,213 A | 5/1977 | Stein |
| 4,027,776 A | 6/1977 | Douglas |
| 4,064,962 A | 12/1977 | Hunt |
| 4,116,197 A | 9/1978 | Bermingham |
| 4,180,178 A | 12/1979 | Turner |
| 4,187,953 A | 2/1980 | Turner |
| 4,194,508 A | 3/1980 | Anderson |
| 4,200,102 A | 4/1980 | Duhamel et al. |
| 4,202,058 A | 5/1980 | Anderson |
| 4,203,503 A | 5/1980 | Bertotti et al. |
| 4,209,076 A | 6/1980 | Bertotti et al. |
| 4,233,025 A | 11/1980 | Larson et al. |
| 4,233,978 A | 11/1980 | Hickey |
| 4,246,901 A | 1/1981 | Frosch et al. |
| 4,253,542 A | 3/1981 | Ruspa et al. |
| 4,257,418 A | 3/1981 | Hessner |
| 4,270,539 A | 6/1981 | Frosch et al. |
| 4,281,655 A | 8/1981 | Terauchi |
| 4,292,916 A | 10/1981 | Bradley et al. |
| 4,330,239 A | 5/1982 | Gannaway |
| 4,352,356 A | 10/1982 | Tong |
| 4,360,933 A | 11/1982 | Kimura et al. |
| 4,365,363 A | 12/1982 | Windauer |
| 4,375,841 A | 3/1983 | Vielbig |
| 4,387,726 A | 6/1983 | Denard |
| 4,425,130 A | 1/1984 | Desmarais |
| 4,446,986 A | 5/1984 | Bowen et al. |
| 4,453,938 A | 6/1984 | Brendling |
| 4,457,314 A | 7/1984 | Knowles |
| 4,476,879 A | 10/1984 | Jackson |
| 4,526,688 A | 7/1985 | Schmidt et al. |
| 4,528,703 A | 7/1985 | Kraus |
| D280,438 S | 9/1985 | Wendt |
| 4,551,141 A | 11/1985 | Mcneil |
| 4,553,968 A | 11/1985 | Komis |
| 4,581,026 A | 4/1986 | Schneider |
| 4,589,516 A | 5/1986 | Inoue et al. |
| 4,601,716 A | 7/1986 | Smith |
| 4,610,675 A | 9/1986 | Triunfol |
| 4,620,333 A | 11/1986 | Ritter |
| 4,626,250 A | 12/1986 | Schneider |
| 4,627,846 A | 12/1986 | Ternstroem |
| 4,631,061 A | 12/1986 | Martin |
| 4,650,477 A | 3/1987 | Johnson |
| 4,655,754 A | 4/1987 | Richmond et al. |
| 4,656,675 A | 4/1987 | Fajnsztajn |
| 4,681,570 A | 7/1987 | Dalton |
| 4,681,577 A | 7/1987 | Stern et al. |
| 4,692,160 A | 9/1987 | Nussbaumer |
| 4,707,864 A | 11/1987 | Ikematsu et al. |
| 4,713,065 A | 12/1987 | Koot |
| 4,713,066 A | 12/1987 | Komis |
| 4,723,953 A * | 2/1988 | Rosenbaum ...... A61F 13/53743 604/374 |
| 4,735,841 A | 4/1988 | Sourdet |
| 4,743,236 A | 5/1988 | Manschot |
| 4,747,166 A | 5/1988 | Kuntz |
| 4,752,944 A | 6/1988 | Conrads et al. |
| 4,769,215 A | 9/1988 | Ehrenkranz |
| 4,771,484 A | 9/1988 | Mozell |
| 4,772,280 A | 9/1988 | Rooyakkers |
| 4,790,830 A | 12/1988 | Hamacher |
| 4,790,835 A | 12/1988 | Elias |
| 4,791,686 A | 12/1988 | Taniguchi et al. |
| 4,795,449 A | 1/1989 | Schneider et al. |
| 4,798,603 A | 1/1989 | Meyer et al. |
| 4,799,928 A | 1/1989 | Crowley |
| 4,804,377 A | 2/1989 | Hanifl et al. |
| 4,812,053 A | 3/1989 | Bhattacharjee |
| 4,813,943 A | 3/1989 | Smith |
| 4,820,297 A | 4/1989 | Kaufman et al. |
| 4,846,818 A | 7/1989 | Keldahl et al. |
| 4,846,909 A | 7/1989 | Klug et al. |
| 4,865,595 A | 9/1989 | Heyden |
| 4,880,417 A | 11/1989 | Yabrov et al. |
| 4,882,794 A | 11/1989 | Stewart |
| 4,883,465 A | 11/1989 | Brennan |
| 4,886,498 A | 12/1989 | Newton |
| 4,886,508 A | 12/1989 | Washington |
| 4,886,509 A | 12/1989 | Mattsson |
| 4,889,532 A | 12/1989 | Metz et al. |
| 4,889,533 A | 12/1989 | Beecher |
| 4,890,691 A | 1/1990 | Ching-ho |
| 4,903,254 A | 2/1990 | Haas |
| 4,904,248 A | 2/1990 | Vaillancourt |
| 4,905,692 A | 3/1990 | More |
| 4,936,838 A | 6/1990 | Cross et al. |
| 4,955,922 A | 9/1990 | Terauchi |
| 4,957,487 A | 9/1990 | Gerow |
| 4,965,460 A | 10/1990 | Tanaka et al. |
| 4,987,849 A | 1/1991 | Sherman |
| 5,002,541 A | 3/1991 | Conkling et al. |
| 5,004,463 A | 4/1991 | Nigay |
| 5,031,248 A | 7/1991 | Kemper |

(56) References Cited

U.S. PATENT DOCUMENTS

| | | |
|---|---|---|
| 5,045,077 A | 9/1991 | Blake |
| 5,045,283 A | 9/1991 | Patel |
| 5,049,144 A | 9/1991 | Payton |
| 5,053,339 A | 10/1991 | Patel |
| 5,057,092 A | 10/1991 | Webster |
| 5,058,088 A | 10/1991 | Haas et al. |
| 5,071,347 A | 12/1991 | Mcguire |
| 5,078,707 A | 1/1992 | Peter |
| 5,084,037 A | 1/1992 | Barnett |
| 5,100,396 A | 3/1992 | Zamierowski |
| 5,112,324 A | 5/1992 | Wallace |
| 5,147,301 A | 9/1992 | Ruvio |
| 5,176,667 A | 1/1993 | Debring |
| 5,195,997 A | 3/1993 | Carns |
| 5,196,654 A | 3/1993 | Diflora et al. |
| 5,203,699 A | 4/1993 | Mcguire |
| 5,244,458 A | 9/1993 | Takasu |
| 5,246,454 A | 9/1993 | Peterson |
| 5,267,988 A | 12/1993 | Farkas |
| 5,275,307 A | 1/1994 | Freese |
| 5,294,983 A | 3/1994 | Ersoz et al. |
| 5,295,983 A | 3/1994 | Kubo |
| 5,300,052 A | 4/1994 | Kubo |
| 5,304,749 A | 4/1994 | Crandell |
| 5,312,383 A | 5/1994 | Kubalak |
| 5,318,550 A | 6/1994 | Cermak et al. |
| 5,330,459 A * | 7/1994 | Lavon ................ A61F 13/495 604/385.12 |
| 5,340,840 A | 8/1994 | Park et al. |
| 5,382,244 A | 1/1995 | Telang |
| 5,409,014 A | 4/1995 | Napoli et al. |
| 5,411,495 A | 5/1995 | Willingham |
| 5,423,784 A | 6/1995 | Metz |
| 5,456,246 A | 10/1995 | Schmieding et al. |
| 5,466,229 A | 11/1995 | Elson et al. |
| 5,478,334 A | 12/1995 | Bernstein |
| 5,499,977 A | 3/1996 | Marx |
| 5,543,042 A | 8/1996 | Filan et al. |
| D373,928 S | 9/1996 | Green |
| 5,582,604 A * | 12/1996 | Ahr ................ A61F 13/495 604/385.12 |
| 5,592,950 A | 1/1997 | Kopelowicz |
| 5,605,161 A | 2/1997 | Cross |
| 5,618,277 A | 4/1997 | Goulter |
| 5,628,735 A | 5/1997 | Skow |
| 5,636,643 A | 6/1997 | Argenta et al. |
| 5,637,104 A | 6/1997 | Ball et al. |
| 5,674,212 A | 10/1997 | Osborn et al. |
| 5,678,564 A | 10/1997 | Lawrence et al. |
| 5,678,654 A | 10/1997 | Uzawa |
| 5,687,429 A | 11/1997 | Rahlff |
| 5,695,485 A | 12/1997 | Duperret et al. |
| 5,700,254 A | 12/1997 | Mcdowall et al. |
| 5,705,777 A | 1/1998 | Flanigan et al. |
| 5,752,944 A | 5/1998 | Dann et al. |
| 5,772,644 A | 6/1998 | Bark et al. |
| 5,792,132 A | 8/1998 | Garcia |
| 5,827,243 A | 10/1998 | Palestrant |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,859,393 A | 1/1999 | Cummins et al. |
| 5,865,378 A | 2/1999 | Hollinshead et al. |
| 5,876,393 A * | 3/1999 | Ahr ................ A61F 13/495 604/385.12 |
| 5,887,291 A | 3/1999 | Bellizzi |
| 5,891,125 A * | 4/1999 | Plumley ............. A61F 13/47 604/385.12 |
| 5,894,608 A | 4/1999 | Birbara |
| D409,303 S | 5/1999 | Oepping |
| 5,911,222 A | 6/1999 | Lawrence et al. |
| 5,957,904 A | 9/1999 | Holland |
| 5,968,026 A | 10/1999 | Osborn et al. |
| 5,972,505 A | 10/1999 | Phillips et al. |
| 6,039,060 A | 3/2000 | Rower |
| 6,050,983 A | 4/2000 | Moore et al. |
| 6,059,762 A | 5/2000 | Boyer et al. |
| 6,063,064 A | 5/2000 | Tuckey et al. |
| 6,098,625 A | 8/2000 | Winkler |
| 6,105,174 A | 8/2000 | Karlsten et al. |
| 6,113,582 A | 9/2000 | Dwork |
| 6,117,163 A | 9/2000 | Bierman |
| 6,123,398 A | 9/2000 | Arai et al. |
| 6,129,718 A | 10/2000 | Wada et al. |
| 6,131,964 A | 10/2000 | Sareshwala |
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,220,050 B1 | 4/2001 | Cooksey |
| 6,244,311 B1 | 6/2001 | Hand et al. |
| 6,248,096 B1 | 6/2001 | Dwork et al. |
| 6,263,887 B1 | 7/2001 | Dunn |
| 6,283,246 B1 | 9/2001 | Nishikawa |
| 6,311,339 B1 | 11/2001 | Kraus |
| 6,336,919 B1 | 1/2002 | Davis et al. |
| 6,338,729 B1 | 1/2002 | Wada et al. |
| 6,352,525 B1 | 3/2002 | Wakabayashi |
| 6,394,988 B1 | 5/2002 | Hashimoto |
| 6,398,742 B1 | 6/2002 | Kim |
| 6,406,463 B1 | 6/2002 | Brown |
| 6,409,712 B1 | 6/2002 | Dutari et al. |
| 6,416,500 B1 | 7/2002 | Wada et al. |
| 6,423,045 B1 * | 7/2002 | Wise ................ A61F 13/47218 604/385.12 |
| 6,428,521 B1 | 8/2002 | Droll |
| 6,428,522 B1 * | 8/2002 | DiPalma ............. A61F 13/4702 604/385.01 |
| 6,446,454 B1 | 9/2002 | Lee et al. |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,524,292 B1 * | 2/2003 | DiPalma ............. A61F 13/47263 604/385.12 |
| 6,540,729 B1 | 4/2003 | Wada et al. |
| 6,547,771 B2 | 4/2003 | Robertson et al. |
| 6,569,133 B2 | 5/2003 | Cheng et al. |
| D476,518 S | 7/2003 | Doppelt |
| 6,592,560 B2 | 7/2003 | Snyder et al. |
| 6,610,038 B1 * | 8/2003 | DiPalma ............. A61F 13/4702 604/385.12 |
| 6,618,868 B2 | 9/2003 | Minnick |
| 6,620,142 B1 | 9/2003 | Flueckiger |
| 6,629,651 B1 | 10/2003 | Male et al. |
| 6,635,038 B2 | 10/2003 | Scovel |
| 6,652,495 B1 | 11/2003 | Walker |
| 6,666,850 B1 * | 12/2003 | Ahr ................ A61F 13/495 604/385.12 |
| 6,685,684 B1 | 2/2004 | Falconer |
| 6,695,828 B1 * | 2/2004 | DiPalma ............. A61F 13/84 604/385.12 |
| 6,700,034 B1 * | 3/2004 | Lindsay ............. A61F 13/53704 604/378 |
| 6,702,793 B1 | 3/2004 | Sweetser et al. |
| 6,706,027 B2 | 3/2004 | Harvie et al. |
| 6,732,384 B2 | 5/2004 | Scott |
| 6,736,977 B1 | 5/2004 | Hall et al. |
| 6,740,066 B2 | 5/2004 | Wolff et al. |
| 6,764,477 B1 | 7/2004 | Chen et al. |
| 6,783,519 B2 | 8/2004 | Samuelsson |
| 6,796,974 B2 | 9/2004 | Palumbo et al. |
| 6,814,547 B2 | 11/2004 | Childers et al. |
| 6,849,065 B2 | 2/2005 | Schmidt et al. |
| 6,857,137 B2 | 2/2005 | Otto |
| 6,885,690 B2 | 4/2005 | Aggerstam et al. |
| 6,888,044 B2 | 5/2005 | Fell et al. |
| 6,893,425 B2 | 5/2005 | Dunn et al. |
| 6,912,737 B2 | 7/2005 | Ernest et al. |
| 6,918,899 B2 | 7/2005 | Harvie |
| 6,979,324 B2 | 12/2005 | Byordi et al. |
| 7,018,366 B2 | 3/2006 | Easter |
| 7,066,411 B2 | 6/2006 | Male et al. |

(56) References Cited

U.S. PATENT DOCUMENTS

| | | |
|---|---|---|
| 7,122,023 B1 | 10/2006 | Hinoki |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,160,273 B2 | 1/2007 | Greter et al. |
| 7,171,699 B2 | 2/2007 | Ernest et al. |
| 7,171,871 B2 | 2/2007 | Kozak |
| 7,179,951 B2 | 2/2007 | Krishnaswamy-mirle et al. |
| 7,181,781 B1 | 2/2007 | Trabold et al. |
| 7,186,245 B1 | 3/2007 | Cheng et al. |
| 7,192,424 B2 | 3/2007 | Cooper |
| 7,219,764 B1 | 5/2007 | Forbes |
| 7,220,250 B2 | 5/2007 | Suzuki et al. |
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,438,706 B2 | 10/2008 | Koizumi et al. |
| 7,488,310 B2 | 2/2009 | Yang |
| 7,491,194 B1 | 2/2009 | Oliwa |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,549,512 B2 | 6/2009 | Newberry |
| 7,585,293 B2 | 9/2009 | Vermaak |
| 7,588,560 B1 | 9/2009 | Dunlop |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 * | 7/2010 | Tazoe .................. A61F 5/451 604/320 |
| 7,755,497 B2 | 7/2010 | Wada et al. |
| 7,766,887 B2 | 8/2010 | Burns et al. |
| D625,407 S | 10/2010 | Koizumi et al. |
| 7,806,879 B2 | 10/2010 | Brooks et al. |
| 7,811,272 B2 | 10/2010 | Lindsay et al. |
| 7,815,067 B2 | 10/2010 | Matsumoto et al. |
| 7,833,169 B2 | 11/2010 | Hannon |
| 7,857,806 B2 | 12/2010 | Karpowicz et al. |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,015,627 B2 | 9/2011 | Baker et al. |
| 8,016,071 B1 | 9/2011 | Martinus et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,353,074 B2 | 1/2013 | Krebs |
| 8,353,886 B2 | 1/2013 | Bester et al. |
| D676,241 S | 2/2013 | Merrill |
| 8,388,588 B2 | 3/2013 | Wada et al. |
| D679,807 S | 4/2013 | Burgess et al. |
| 8,425,482 B2 | 4/2013 | Khoubnazar |
| 8,434,586 B2 | 5/2013 | Pawelski et al. |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,500,719 B1 | 8/2013 | Simpson et al. |
| 8,512,301 B2 | 8/2013 | Ma |
| 8,529,530 B2 | 9/2013 | Koch et al. |
| 8,535,284 B2 | 9/2013 | Joder et al. |
| 8,546,639 B2 | 10/2013 | Wada et al. |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,652,112 B2 | 2/2014 | Johannison et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,145,879 B2 | 9/2015 | Pirovano et al. |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,233,020 B2 | 1/2016 | Matsumiya |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,381,108 B2 | 7/2016 | Longoni et al. |
| 9,382,047 B2 | 7/2016 | Schmidtner et al. |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| 9,623,159 B2 | 4/2017 | Locke |
| D789,522 S | 6/2017 | Burgess et al. |
| 9,687,849 B2 | 6/2017 | Bruno et al. |
| 9,694,949 B2 | 7/2017 | Hendricks et al. |
| 9,709,048 B2 | 7/2017 | Kinjo |
| 9,713,547 B2 | 7/2017 | Lee et al. |
| 9,732,754 B2 | 8/2017 | Huang et al. |
| 9,752,564 B2 | 9/2017 | Arceno et al. |
| 9,788,992 B2 | 10/2017 | Harvie |
| D804,907 S | 12/2017 | Sandoval |
| 9,868,564 B2 | 1/2018 | Mcgirr et al. |
| D814,239 S | 4/2018 | Arora |
| D817,484 S | 5/2018 | Lafond |

(56) References Cited

U.S. PATENT DOCUMENTS

| | | |
|---|---|---|
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 | 3/2019 | Sanchez et al. |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Villarreal |
| 10,407,222 B2 | 9/2019 | Allen |
| 10,478,356 B2 | 11/2019 | Griffin |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| RE47,930 E | 4/2020 | Cho |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B1 | 10/2020 | Harrison |
| D901,214 S | 11/2020 | Hu |
| 10,857,025 B2 | 12/2020 | Davis et al. |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,378 B2 | 4/2021 | Ryu et al. |
| 10,973,678 B2 | 4/2021 | Newton et al. |
| 10,974,874 B2 | 4/2021 | Ragias et al. |
| 11,000,401 B2 | 5/2021 | Ecklund et al. |
| D923,365 S | 6/2021 | Wang |
| 11,026,829 B2 | 6/2021 | Harvie |
| 11,027,900 B2 | 6/2021 | Liu |
| 11,045,346 B2 | 6/2021 | Argent et al. |
| D928,946 S | 8/2021 | Sanchez et al. |
| 11,168,420 B2 | 11/2021 | Kinugasa et al. |
| 11,179,506 B2 | 11/2021 | Barr et al. |
| 11,226,376 B2 | 1/2022 | Yamauchi et al. |
| 11,326,586 B2 | 5/2022 | Milner et al. |
| 11,369,508 B2 | 6/2022 | Ecklund et al. |
| 11,376,152 B2 | 7/2022 | Sanchez et al. |
| 11,382,786 B2 | 7/2022 | Sanchez et al. |
| 11,382,788 B2 * | 7/2022 | Hjorth .................. A61F 5/4553 |
| 11,389,318 B2 | 7/2022 | Radl et al. |
| 11,395,871 B2 | 7/2022 | Radl et al. |
| 11,426,303 B2 | 8/2022 | Davis et al. |
| 11,504,265 B2 | 11/2022 | Godinez et al. |
| 11,529,252 B2 | 12/2022 | Glithero et al. |
| 11,547,788 B2 | 1/2023 | Radl et al. |
| 11,806,266 B2 | 11/2023 | Sanchez et al. |
| D1,010,109 S | 1/2024 | Ecklund et al. |
| 11,857,716 B2 | 1/2024 | Lee et al. |
| 11,890,221 B2 | 2/2024 | Ulreich et al. |
| 11,925,575 B2 | 3/2024 | Newton |
| 2001/0037097 A1 * | 11/2001 | Cheng .................. A61F 5/455 4/144.1 |
| 2001/0054426 A1 | 12/2001 | Knudson et al. |
| 2002/0019614 A1 | 2/2002 | Woon |
| 2002/0026161 A1 | 2/2002 | Grundke |
| 2002/0087131 A1 | 7/2002 | Wolff et al. |
| 2002/0091364 A1 | 7/2002 | Prabhakar |
| 2002/0189992 A1 | 12/2002 | Schmidt et al. |
| 2002/0193760 A1 | 12/2002 | Thompson |
| 2003/0004436 A1 | 1/2003 | Schmidt et al. |
| 2003/0032931 A1 | 2/2003 | Grundke et al. |
| 2003/0032944 A1 | 2/2003 | Cawood |
| 2003/0073964 A1 | 4/2003 | Palumbo et al. |
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1 * | 10/2003 | Harvie .................. A61F 5/455 604/355 |
| 2003/0204173 A1 | 10/2003 | Burns et al. |
| 2003/0233079 A1 | 12/2003 | Parks et al. |
| 2004/0006321 A1 | 1/2004 | Cheng et al. |
| 2004/0015141 A1 * | 1/2004 | Cheng .................. A61F 5/455 604/329 |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 | 7/2004 | Easter |
| 2004/0147863 A1 * | 7/2004 | Diaz .................. A61F 13/15 602/41 |
| 2004/0147894 A1 | 7/2004 | Mizutani et al. |
| 2004/0158221 A1 | 8/2004 | Mizutani et al. |
| 2004/0176731 A1 | 9/2004 | Cheng et al. |
| 2004/0176746 A1 | 9/2004 | Forral |
| 2004/0191919 A1 | 9/2004 | Unger et al. |
| 2004/0207530 A1 | 10/2004 | Nielsen |
| 2004/0236292 A1 * | 11/2004 | Tazoe .................. A61F 5/451 604/317 |
| 2004/0243075 A1 * | 12/2004 | Harvie .................. A61F 5/451 604/355 |
| 2004/0254547 A1 | 12/2004 | Okabe et al. |
| 2005/0010182 A1 | 1/2005 | Parks et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0119630 A1 * | 6/2005 | Harvie .................. A61F 5/451 604/355 |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0273920 A1 | 12/2005 | Marinas |
| 2005/0277904 A1 | 12/2005 | Chase et al. |
| 2005/0279359 A1 | 12/2005 | LeBlanc et al. |
| 2006/0004332 A1 | 1/2006 | Marx |
| 2006/0015080 A1 * | 1/2006 | Mahnensmith ........... A61F 5/48 604/327 |
| 2006/0015081 A1 | 1/2006 | Suzuki et al. |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0111648 A1 | 5/2006 | Vermaak |
| 2006/0155214 A1 | 7/2006 | Wightman |
| 2006/0171997 A1 * | 8/2006 | Gruenbacher ........... A47K 7/03 424/443 |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 * | 10/2006 | Harvie .................. A61F 5/451 604/355 |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0038194 A1 | 2/2007 | Wada et al. |
| 2007/0055209 A1 | 3/2007 | Patel et al. |
| 2007/0073252 A1 | 3/2007 | Forgrave |

(56) References Cited

U.S. PATENT DOCUMENTS

| | | |
|---|---|---|
| 2007/0117880 A1 | 5/2007 | Elson et al. |
| 2007/0118993 A1* | 5/2007 | Bates .................. A61G 7/1021 5/695 |
| 2007/0135786 A1 | 6/2007 | Schmidt et al. |
| 2007/0137718 A1 | 6/2007 | Rushlander et al. |
| 2007/0149935 A1 | 6/2007 | Dirico |
| 2007/0191804 A1 | 8/2007 | Coley |
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0091153 A1* | 4/2008 | Harvie .................. A61F 5/451 604/318 |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1* | 10/2008 | Collins .................. A61F 13/42 604/361 |
| 2008/0281282 A1 | 11/2008 | Finger et al. |
| 2008/0287894 A1 | 11/2008 | Van Den Heuvel et al. |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0192482 A1 | 7/2009 | Dodge et al. |
| 2009/0234312 A1 | 9/2009 | Otoole et al. |
| 2009/0251510 A1 | 10/2009 | Noro et al. |
| 2009/0264840 A1 | 10/2009 | Virginio |
| 2009/0270822 A1 | 10/2009 | Medeiros |
| 2009/0281510 A1 | 11/2009 | Fisher |
| 2010/0004612 A1 | 1/2010 | Thevenin |
| 2010/0058660 A1 | 3/2010 | Williams |
| 2010/0121289 A1 | 5/2010 | Parks et al. |
| 2010/0160882 A1* | 6/2010 | Lowe .................. A61F 13/505 604/361 |
| 2010/0174250 A1* | 7/2010 | Hu .................. A61F 13/05 602/54 |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060299 A1 | 3/2011 | Wada et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0138064 A1 | 5/2013 | Stroebech et al. |
| 2013/0150813 A1 | 6/2013 | Gordon et al. |
| 2013/0245496 A1 | 9/2013 | Wells et al. |
| 2013/0245586 A1 | 9/2013 | Jha |
| 2013/0292537 A1 | 11/2013 | Dirico |
| 2014/0005647 A1 | 1/2014 | Shuffler et al. |
| 2014/0031774 A1 | 1/2014 | Bengtson |
| 2014/0039432 A1 | 2/2014 | Dunbar et al. |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0374848 A1* | 12/2016 | Sanchez .................. A61F 5/453 604/319 |
| 2017/0007438 A1 | 1/2017 | Harvie |
| 2017/0014560 A1 | 1/2017 | Minskoff et al. |
| 2017/0100276 A1 | 4/2017 | Joh |
| 2017/0128638 A1 | 5/2017 | Giezendanner et al. |

(56) References Cited

U.S. PATENT DOCUMENTS

| | | |
|---|---|---|
| 2017/0143534 A1 | 5/2017 | Sanchez |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1* | 9/2017 | Sanchez ............... A61F 5/4404 |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0042748 A1 | 12/2017 | Griffin |
| 2017/0348139 A1 | 12/2017 | Newton et al. |
| 2017/0354532 A1 | 12/2017 | Holt |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1* | 8/2018 | Davis ..................... A61F 5/451 |
| 2018/0256384 A1 | 9/2018 | Kasirye |
| 2018/0271694 A1 | 9/2018 | Fernandez et al. |
| 2018/0317892 A1 | 11/2018 | Catlin |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0100362 A1 | 4/2019 | Meyers et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0247222 A1 | 8/2019 | Ecklund et al. |
| 2019/0247223 A1* | 8/2019 | Brun ..................... A61F 5/453 |
| 2019/0282391 A1 | 9/2019 | Johannes et al. |
| 2019/0314189 A1* | 10/2019 | Acosta ................... A61F 5/44 |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2020/0008985 A1 | 1/2020 | Nguyen et al. |
| 2020/0030595 A1* | 1/2020 | Boukidjian ............ A61M 27/00 |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-schärli et al. |
| 2020/0129322 A1 | 4/2020 | Leuckel |
| 2020/0171217 A9 | 6/2020 | Braga et al. |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0385179 A1 | 12/2020 | Mccourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0069009 A1 | 3/2021 | Im |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0236324 A1 | 8/2021 | Sweeney |
| 2021/0267787 A1 | 9/2021 | Nazemi |
| 2021/0275343 A1 | 9/2021 | Sanchez et al. |
| 2021/0315727 A1 | 10/2021 | Jiang |
| 2021/0353450 A1 | 11/2021 | Sharma et al. |
| 2021/0361469 A1 | 11/2021 | Liu et al. |
| 2021/0369495 A1* | 12/2021 | Cheng ................... A61F 5/4405 |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0039995 A1 | 2/2022 | Johannes et al. |
| 2022/0047410 A1 | 2/2022 | Walthall |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104981 A1 | 4/2022 | Jones |
| 2022/0117773 A1 | 4/2022 | Davis et al. |
| 2022/0117774 A1 | 4/2022 | Meyer et al. |
| 2022/0117775 A1 | 4/2022 | Jones et al. |
| 2022/0133524 A1 | 5/2022 | Davis |
| 2022/0151817 A1 | 5/2022 | Mann |
| 2022/0160949 A1 | 5/2022 | Simiele et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |
| 2022/0257407 A1 | 8/2022 | Johannes et al. |
| 2022/0265460 A1 | 8/2022 | Coker |
| 2022/0265462 A1 | 8/2022 | Alder et al. |
| 2022/0270711 A1 | 8/2022 | Feala et al. |
| 2022/0273482 A1 | 9/2022 | Johannes et al. |
| 2022/0280357 A1 | 9/2022 | Jagannathan et al. |
| 2022/0287689 A1 | 9/2022 | Johannes |
| 2022/0296408 A1 | 9/2022 | Evans et al. |
| 2022/0305191 A1 | 9/2022 | Joseph et al. |
| 2022/0313222 A1 | 10/2022 | Austermann et al. |
| 2022/0313474 A1 | 10/2022 | Kriscovich et al. |
| 2022/0331170 A1 | 10/2022 | Erdem et al. |
| 2022/0339024 A1 | 10/2022 | Johannes et al. |
| 2022/0354685 A1 | 11/2022 | Davis et al. |

(56) References Cited

U.S. PATENT DOCUMENTS

| | | |
|---|---|---|
| 2022/0362049 A1 | 11/2022 | Austermann et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0395390 A1 | 12/2022 | Brooks |
| 2022/0395391 A1 | 12/2022 | Saunders et al. |
| 2023/0018845 A1 | 1/2023 | Lee |
| 2023/0020563 A1 | 1/2023 | Sharma et al. |
| 2023/0031640 A1 | 2/2023 | Hughett et al. |
| 2023/0037159 A1 | 2/2023 | Brennan et al. |
| 2023/0052238 A1 | 2/2023 | Oluwasogo |
| 2023/0062994 A1 | 3/2023 | Ecklund et al. |
| 2023/0070347 A1 | 3/2023 | Watson et al. |
| 2023/0073708 A1 | 3/2023 | Xu et al. |
| 2023/0089032 A1 | 3/2023 | Hughett et al. |
| 2023/0099821 A1 | 3/2023 | Radl et al. |
| 2023/0105001 A1 | 4/2023 | Whittome et al. |
| 2023/0138269 A1 | 5/2023 | Abdelal et al. |
| 2023/0145365 A1 | 5/2023 | Martin et al. |
| 2023/0210504 A1 | 7/2023 | Kuroda et al. |
| 2023/0218426 A1 | 7/2023 | Hughett |
| 2023/0248562 A1 | 8/2023 | Sanchez et al. |
| 2023/0255812 A1 | 8/2023 | Sanchez et al. |
| 2023/0255813 A1 | 8/2023 | Sanchez et al. |
| 2023/0255815 A1 | 8/2023 | Newton |
| 2023/0263650 A1 | 8/2023 | Sanchez et al. |
| 2023/0263655 A1 | 8/2023 | Johannes et al. |
| 2023/0277362 A1 | 9/2023 | Davis et al. |
| 2023/0293339 A1 | 9/2023 | James |
| 2023/0301846 A1 | 9/2023 | Greenwood |
| 2023/0355423 A1 | 11/2023 | Stevenson et al. |
| 2023/0404791 A1 | 12/2023 | Ecklund et al. |
| 2024/0009023 A1 | 1/2024 | Johannes et al. |
| 2024/0041638 A1 | 2/2024 | Johannes et al. |
| 2024/0058161 A1 | 2/2024 | Ulreich et al. |

FOREIGN PATENT DOCUMENTS

| | | |
|---|---|---|
| CA | 2165286 C | 9/1999 |
| CA | 2354132 A1 | 6/2000 |
| CA | 2488867 C | 8/2007 |
| CA | 3050918 A1 | 8/2018 |
| CA | 3098571 A1 | 11/2019 |
| CN | 2269203 Y | 12/1997 |
| CN | 1332620 A | 1/2002 |
| CN | 1533755 A | 10/2004 |
| CN | 1602825 A | 4/2005 |
| CN | 1720888 A | 1/2006 |
| CN | 2936204 Y | 8/2007 |
| CN | 101262836 A | 9/2008 |
| CN | 101522148 A | 9/2009 |
| CN | 102159159 A | 8/2011 |
| CN | 202184840 U | 4/2012 |
| CN | 102481441 A | 5/2012 |
| CN | 202463712 U | 10/2012 |
| CN | 103533968 A | 1/2014 |
| CN | 103717180 A | 4/2014 |
| CN | 204562697 U | 8/2015 |
| CN | 105411783 A | 3/2016 |
| CN | 105451693 A | 3/2016 |
| CN | 105534632 A * | 5/2016 |
| CN | 205849719 U | 1/2017 |
| CN | 106726089 A * | 5/2017 |
| CN | 107847384 A | 3/2018 |
| CN | 107920912 A | 4/2018 |
| CN | 209285902 U | 8/2019 |
| CN | 110381883 A | 10/2019 |
| CN | 211198839 U | 8/2020 |
| CN | 112566550 A | 3/2021 |
| CN | 112603184 A | 4/2021 |
| CN | 114007493 A | 2/2022 |
| CN | 114375187 A | 4/2022 |
| CN | 116096332 A | 5/2023 |
| DE | 1516466 A1 | 6/1969 |
| DE | 2721330 A1 | 11/1977 |
| DE | 2742298 A1 | 3/1978 |
| DE | 9407554.9 U1 | 5/1995 |
| DE | 4443710 A1 | 6/1995 |
| DE | 4416094 A1 | 11/1995 |
| DE | 4236097 C2 | 10/1996 |
| DE | 19619597 A1 | 11/1997 |
| DE | 102005037762 B3 | 9/2006 |
| DE | 102011103783 A1 | 12/2012 |
| DE | 202015104597 U1 | 7/2016 |
| DK | 9600118 | 11/1996 |
| EP | 0032138 A2 | 7/1981 |
| EP | 0066070 B1 | 12/1982 |
| EP | 0140470 A1 | 5/1985 |
| EP | 0140471 B1 | 5/1988 |
| EP | 0274753 A2 | 7/1988 |
| EP | 0119143 B1 | 11/1988 |
| EP | 0483592 A1 | 5/1992 |
| EP | 0610638 A1 | 8/1994 |
| EP | 0613355 A1 | 9/1994 |
| EP | 0613355 B1 | 1/1997 |
| EP | 0787472 A1 | 8/1997 |
| EP | 0966936 A1 | 12/1999 |
| EP | 0987293 A1 | 3/2000 |
| EP | 1063953 A1 | 1/2001 |
| EP | 0653928 B1 | 10/2002 |
| EP | 1332738 A1 | 8/2003 |
| EP | 1382318 A1 | 1/2004 |
| EP | 1089684 B1 | 10/2004 |
| EP | 1616542 A1 | 1/2006 |
| EP | 1382318 B1 | 5/2006 |
| EP | 1063953 B1 | 1/2007 |
| EP | 1872752 A1 | 1/2008 |
| EP | 2180907 A1 | 5/2010 |
| EP | 2380532 A1 | 10/2011 |
| EP | 2389908 A1 | 11/2011 |
| EP | 2601916 A1 | 6/2013 |
| EP | 2676643 A1 | 12/2013 |
| EP | 2997950 A2 | 3/2016 |
| EP | 2879534 B1 | 3/2017 |
| EP | 3424471 A1 | 1/2019 |
| EP | 3169292 B1 | 11/2019 |
| EP | 3787570 B1 | 3/2020 |
| EP | 3753492 A1 | 12/2020 |
| EP | 3788992 A1 | 3/2021 |
| EP | 3576689 B1 | 3/2022 |
| EP | 3752110 B1 | 3/2022 |
| EP | 4025163 A1 | 7/2022 |
| EP | 3463180 B1 | 3/2023 |
| GB | 1011517 A | 12/1965 |
| GB | 1467144 A | 3/1977 |
| GB | 2106395 A | 4/1983 |
| GB | 2106784 A | 4/1983 |
| GB | 2148126 A | 5/1985 |
| GB | 2171315 A | 8/1986 |
| GB | 2181953 A | 5/1987 |
| GB | 2148126 B | 7/1987 |
| GB | 2191095 A | 12/1987 |
| GB | 2199750 A | 7/1988 |
| GB | 2260907 A | 5/1993 |
| GB | 2462267 A | 2/2010 |
| GB | 2469496 A | 10/2010 |
| GB | 2490327 A | 10/2012 |
| GB | 2507318 A | 4/2014 |
| GB | 2612752 A | 5/2023 |
| IT | 201800009129 A1 | 4/2020 |
| JP | S5410596 A | 1/1979 |
| JP | S5410596 Y2 | 5/1979 |
| JP | S55155618 A | 12/1980 |
| JP | S5888596 U | 6/1983 |
| JP | S63107780 U | 7/1988 |
| JP | H0267530 A | 3/1990 |
| JP | H02103871 A | 4/1990 |
| JP | H02131422 A | 5/1990 |
| JP | H02131422 U | 11/1990 |
| JP | H0460220 A | 2/1992 |
| JP | H05123349 A | 5/1993 |
| JP | H05123350 A | 5/1993 |

(56) References Cited

FOREIGN PATENT DOCUMENTS

| | | |
|---|---|---|
| JP | 3087938 B2 | 10/1995 |
| JP | H085630 A | 1/1996 |
| JP | H1040141 A | 2/1998 |
| JP | H10225430 A | 8/1998 |
| JP | H11113946 A | 4/1999 |
| JP | H11290365 A | 10/1999 |
| JP | 2000116690 A | 4/2000 |
| JP | 2000185068 A | 7/2000 |
| JP | 2001054531 A | 2/2001 |
| JP | 2001070331 A | 3/2001 |
| JP | 2001224616 A | 8/2001 |
| JP | 2001276107 A | 10/2001 |
| JP | 2001276108 A | 10/2001 |
| JP | 2002028173 A | 1/2002 |
| JP | 2003505152 A | 2/2003 |
| JP | 2003180722 A | 7/2003 |
| JP | 2004130056 A | 4/2004 |
| JP | 2004267530 A | 9/2004 |
| JP | 2005066011 A | 3/2005 |
| JP | 2005066325 A | 3/2005 |
| JP | 2005518237 A | 6/2005 |
| JP | 3749097 B2 | 12/2005 |
| JP | 2006026108 A | 2/2006 |
| JP | 3123547 B2 | 6/2006 |
| JP | 2006136492 A | 6/2006 |
| JP | 2006204868 A | 8/2006 |
| JP | 2007044494 A | 2/2007 |
| JP | 3132659 B2 | 5/2007 |
| JP | 4039641 B2 | 11/2007 |
| JP | 2009509570 A | 3/2009 |
| JP | 2010081981 A | 4/2010 |
| JP | 4640772 B2 | 12/2010 |
| JP | 2010536439 A | 12/2010 |
| JP | 4747166 B2 | 5/2011 |
| JP | 2011087823 A | 5/2011 |
| JP | 4801218 B1 | 8/2011 |
| JP | 2011218130 A | 11/2011 |
| JP | 2011224070 A | 11/2011 |
| JP | 2012523869 A | 10/2012 |
| JP | 2013238608 A | 11/2013 |
| JP | 2014521960 A | 8/2014 |
| JP | 2015092945 A | 5/2015 |
| JP | 3198994 B2 | 7/2015 |
| JP | 2019525811 A | 9/2019 |
| JP | 2021120686 A | 8/2021 |
| JP | 2021522009 A | 8/2021 |
| JP | 7129493 B2 | 8/2022 |
| JP | 2023532132 A | 7/2023 |
| KR | 200290061 Y1 | 9/2002 |
| KR | 20030047451 A | 6/2003 |
| KR | 20140039485 A | 4/2014 |
| KR | 101432639 B1 | 8/2014 |
| KR | 20180106659 A | 10/2018 |
| KR | 20180108774 A | 10/2018 |
| PT | 2068717 E | 6/2013 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9307839 A1 | 4/1993 |
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0069377 A1 | 11/2000 |
| WO | 0079497 A1 | 12/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2005051252 A1 | 6/2005 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2006037140 A2 | 4/2006 |
| WO | 2007005851 A2 | 1/2007 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009052502 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013082397 A1 | 6/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016124203 A1 | 8/2016 |
| WO | 2016139448 A1 | 9/2016 |
| WO | 2016166562 A1 | 10/2016 |
| WO | 2016167535 A1 | 10/2016 |

(56) References Cited

FOREIGN PATENT DOCUMENTS

| | | |
|---|---|---|
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017001532 A2 | 1/2017 |
| WO | 2017075226 A1 | 5/2017 |
| WO | 2017152198 A1 | 9/2017 |
| WO | 2017153357 A1 | 9/2017 |
| WO | 2017162559 A1 | 9/2017 |
| WO | 2017205446 A1 | 11/2017 |
| WO | 2017209779 A1 | 12/2017 |
| WO | 2017210524 A1 | 12/2017 |
| WO | 2018022414 A1 | 2/2018 |
| WO | 2018044781 A1 | 3/2018 |
| WO | 2018056953 A1 | 3/2018 |
| WO | 2018090550 A1 | 3/2018 |
| WO | 2018138513 A1 | 8/2018 |
| WO | 2018144318 A1 | 8/2018 |
| WO | 2018144463 A1 | 8/2018 |
| WO | 2018150263 A1 | 8/2018 |
| WO | 2018150268 A1 | 8/2018 |
| WO | 2018152156 A1 | 8/2018 |
| WO | 2018183791 A1 | 10/2018 |
| WO | 2018150267 A3 | 11/2018 |
| WO | 2018235026 A1 | 12/2018 |
| WO | 2018235065 A1 | 12/2018 |
| WO | 2019004404 A1 | 1/2019 |
| WO | 2019041005 A1 | 3/2019 |
| WO | 2019044217 A1 | 3/2019 |
| WO | 2019044218 A1 | 3/2019 |
| WO | 2019044219 A1 | 3/2019 |
| WO | 2019065541 A1 | 4/2019 |
| WO | 2019096845 A1 | 5/2019 |
| WO | 2019150385 A1 | 8/2019 |
| WO | 2019161094 A1 | 8/2019 |
| WO | 2019188566 A1 | 10/2019 |
| WO | 2019190593 A1 | 10/2019 |
| WO | 2019212949 A1 | 11/2019 |
| WO | 2019212950 A1 | 11/2019 |
| WO | 2019212951 A1 | 11/2019 |
| WO | 2019212952 A1 | 11/2019 |
| WO | 2019212955 A1 | 11/2019 |
| WO | 2019212956 A1 | 11/2019 |
| WO | 2019214787 A1 | 11/2019 |
| WO | 2019214788 A1 | 11/2019 |
| WO | 2019226826 A1 | 11/2019 |
| WO | WO-2019239433 A1 * | 12/2019 |
| WO | 2020000994 A1 | 1/2020 |
| WO | 2020020618 A1 | 1/2020 |
| WO | 2020038822 A1 | 1/2020 |
| WO | 2020088409 A1 | 5/2020 |
| WO | 2020049394 A3 | 6/2020 |
| WO | 2020120657 A1 | 6/2020 |
| WO | 2020152575 A1 | 7/2020 |
| WO | 2020182923 A1 | 9/2020 |
| WO | 2020204967 A1 | 10/2020 |
| WO | 2020205939 A1 | 10/2020 |
| WO | 2020209898 A1 | 10/2020 |
| WO | 2020242790 A1 | 12/2020 |
| WO | 2020251893 A1 | 12/2020 |
| WO | 2020256865 A1 | 12/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016300 A1 | 1/2021 |
| WO | 2021025919 A1 | 2/2021 |
| WO | 2021034886 A1 | 2/2021 |
| WO | 2021041123 A1 | 3/2021 |
| WO | 2021046501 A1 | 3/2021 |
| WO | 2021086868 A1 | 5/2021 |
| WO | 2021094352 A1 | 5/2021 |
| WO | 2021094639 A1 | 5/2021 |
| WO | 2021102296 A1 | 5/2021 |
| WO | 2021107025 A1 | 6/2021 |
| WO | 2021138411 A1 | 7/2021 |
| WO | 2021138414 A1 | 7/2021 |
| WO | 2021154686 A1 | 8/2021 |
| WO | 2021155206 A1 | 8/2021 |
| WO | 2021173436 A1 | 9/2021 |
| WO | 2021188817 A1 | 9/2021 |
| WO | 2021195384 A1 | 9/2021 |
| WO | 2021205995 A1 | 10/2021 |
| WO | 2021207621 A1 | 10/2021 |
| WO | 2021211568 A1 | 10/2021 |
| WO | 2021211801 A1 | 10/2021 |
| WO | 2021216419 A1 | 10/2021 |
| WO | 2021216422 A1 | 10/2021 |
| WO | 2021231532 A1 | 11/2021 |
| WO | 2021247523 A1 | 12/2021 |
| WO | 2021257202 A1 | 12/2021 |
| WO | 2022006256 A1 | 1/2022 |
| WO | 2022031943 A1 | 2/2022 |
| WO | 2022035745 A1 | 2/2022 |
| WO | 2022051360 A1 | 3/2022 |
| WO | 2022054613 A1 | 3/2022 |
| WO | 2022066704 A1 | 3/2022 |
| WO | 2022076427 A2 | 4/2022 |
| WO | 2022086898 A1 | 4/2022 |
| WO | 2022098536 A1 | 5/2022 |
| WO | 2022115692 A1 | 6/2022 |
| WO | 2022125685 A1 | 6/2022 |
| WO | 2022140545 A1 | 6/2022 |
| WO | 2022150360 A1 | 7/2022 |
| WO | 2022150463 A1 | 7/2022 |
| WO | 2022159392 A1 | 7/2022 |
| WO | 2022170182 A1 | 8/2022 |
| WO | 2022182385 A1 | 9/2022 |
| WO | 2022187152 A1 | 9/2022 |
| WO | 2022192188 A1 | 9/2022 |
| WO | 2022192347 A1 | 9/2022 |
| WO | 2022216507 A1 | 10/2022 |
| WO | 2022222030 A1 | 10/2022 |
| WO | 2023014639 A1 | 2/2023 |
| WO | 2023014641 A1 | 2/2023 |
| WO | 2023018475 A2 | 2/2023 |
| WO | 2023034453 A1 | 3/2023 |
| WO | 2023038945 A1 | 3/2023 |
| WO | 2023038950 A1 | 3/2023 |
| WO | 2023049109 A1 | 3/2023 |
| WO | 2023049175 A1 | 3/2023 |
| WO | 2023086394 A1 | 5/2023 |
| WO | 2023149884 A1 | 8/2023 |
| WO | 2023149902 A1 | 8/2023 |
| WO | 2023149903 A1 | 8/2023 |
| WO | 2023154390 A1 | 8/2023 |
| WO | 2023191764 A1 | 10/2023 |
| WO | 2023244238 A1 | 12/2023 |

OTHER PUBLICATIONS

Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.

(56) References Cited

OTHER PUBLICATIONS

Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/899,956 mailed Apr. 19, 2021.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 29/624,661 mailed Aug. 4, 2021.
Non-Final Office Action for U.S. Appl. No. 14/592,591 mailed Mar. 20, 2020.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.

(56) References Cited

OTHER PUBLICATIONS

Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/088,272 mailed Jan. 25, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 17/088,272 mailed Aug. 5, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice to File Missing Parts for U.S. Appl. No. 17/179,116 mailed Mar. 3, 2021.
Restriction Requirement for U.S. Appl. No. 16/478,180 mailed May 25, 2021.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/611,587, filed Jun. 1, 2017.
U.S. Appl. No. 15/612,325, filed Jun. 2, 2017.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/461,036 mailed Aug. 30, 2021.
U.S. Appl. No. 29/741,751, filed Jul. 15, 2020.
U.S. Appl. No. 62/452,437, filed Jan. 31, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/073,545, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/109,066, filed Nov. 3, 2020.
U.S. Appl. No. 63/112,417, filed Nov. 11, 2020.
U.S. Appl. No. 63/119,161, filed Nov. 30, 2020.

(56) References Cited

OTHER PUBLICATIONS

U.S. Appl. No. 63/124,271, filed Dec. 11, 2020.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,210, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/214,551, filed Jun. 24, 2021.
U.S. Appl. No. 63/214,570, filed Jun. 24, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
Defendant and Counterclaim Plaintiff Sage Products, LLC's Answer, Defenses, and Counterclaims to Plaintiff's Amended Complaint, Nov. 1, 2019.
Memorandum Order, Feb. 2021, 14 pgs.
Sage's Initial Invalidity Contentions Regarding U.S. Pat. Nos. 8,287,508; 10,226,375; and 10,390,989, May 29, 2020, 193 pages.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Sage's Second Supplemental Invalidity Contentions Regarding U.S. Pat. Nos. 8,287,508, 10,226,375, 10,390,989, and 10,376,407, 292 pages.
Boehringer CareDry System—Second Generation for Non-Invasive Urinary Management for Females, Mar. 2021, 3 pgs
Excerpts from the 508 (U.S. Pat. No. 8,278,508) Patent's Prosecution History, 2020, 99 pages.
Plaintiff's Opening Claim Construction Brief, Case No. 19-1508-MN, Oct. 16, 2020, 26 pages.
Plaintiff's Identification of Claim Terms and Proposed Constructions, Case No. 19-1508-MN, 3 pages.
PureWick's Response to Interrogatory No. 9 in *PureWick, LLC v. Sage Products, LLC*, Case No. 19-1508-MN, Mar. 23, 2020, 6 pages.
Sage's Preliminary Identification of Claim Elements and Proposed Constructions for U.S. Pat. Nos. 8,287,508, 10,226,376, 10,390,989 and 10,376,407, Case No. 19-1508-MN, 7 pages.
Decision Granting Institution of Inter Partes Review for U.S. Pat. No. 8,287,508, Case No. 2020-01426, Feb. 17, 2021, 39 pages.
Corrected Certificate of Service, Case No. IPR2020-01426, U.S. Pat. No. 8,287,508, 2020, 2 pages.
Declaration of Diane K. Newman Curriculum Vitae, Petition for Interparties Review, 2020, pp. 1-199.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.

"AMXD Control Starter Kit Brochure", https://www.omnimedicalsys.com/index.php?page=products, Omni Medical, 8 pages.
"AMXDmax In-Flight Bladder Relief", Omni Medical; Omni Medical Systems, Inc., 2015.
"AMXDX—Advanced Mission Extender Device Brochure", Omni Medical, Omni Brochure—http://www.omnimedicalsys.com/uploads/AMXDFixedWing.pdf, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, Omni Presentation https://www.omnimedicalsys.com/uploads/AMXDmax_HSD.pdf, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology 2005-06", British Department of Health, Nov. 2006, 40 pages.
"Step by Step How Ur24 WorksHome", http://medicalpatentur24.com, last accessed Dec. 6, 2017, Aug. 30, 2017, 4 pages.
"Underwear that absorbs your period", Thinx!, https://www.shethinx.com/pages/thinx-it-works last accessed Jun. 24, 2020, 7 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, MD&DI, 2014, 4 pages.
Hollister, Female Urinary and Pouch and Male Urinary Pouch Brochure, 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.
Hollister, "Retracted Penis Pouch by Hollister", Vitality Medical.com, https://www.vitalitymedical.com/hollister-retracted-penis-pouch.html last accessed Jun. 24, 2020, 6 pages.
Macaulay, et al., "A Noninvasive Continence Management System: Development and Evaluation of a Novel Toileting Device for Women", The Wound, Ostomy and Continence Nurses Society, vol. 34 No. 6, 2007, pp. 641-648.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Parmar, "10 Finalists Chosen for Dare-to-Dream Medtech Design Challenge (PureWick)", Design Services, Nov. 10, 2014, 3 pages.
Purewick, "Incontinence Relief for Women", Presentation, Sep. 23, 2015, 7 pages.
Pytlik, "Super Absorbent Polymers", University of Buffalo, http://www.courses.sens.buffalo.edu/ce435/Diapers/Diapers.html, accessed on Feb. 17, 2017.
Sachtman, "New Relief for Pilots? It Depends", Wired, https://www.wired.com/2008/05/pilot-relief/, 2008, 2 pages.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Dec. 29, 2023.

(56) References Cited

OTHER PUBLICATIONS

Advisory Action for U.S. Appl. No. 16/433,773 mailed Feb. 15, 2023.
Advisory Action for U.S. Appl. No. 16/449,039 mailed Jan. 25, 2024.
Advisory Action for U.S. Appl. No. 16/452,258 mailed Apr. 8, 2024.
Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/478,180 mailed Sep. 7, 2023.
Advisory Action for U.S. Appl. No. 16/904,868 mailed Jan. 2, 2024.
Advisory Action for U.S. Appl. No. 16/904,868 mailed Jun. 15, 2022.
Advisory Action for U.S. Appl. No. 16/905,400 mailed Feb. 16, 2022.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/446,256 mailed Dec. 8, 2023.
Advisory Action for U.S. Appl. No. 17/446,654 mailed Apr. 15, 2024.
Advisory Action for U.S. Appl. No. 17/448,811 mailed Nov. 15, 2023.
Advisory Action for U.S. Appl. No. 17/450,864 mailed on Mar. 21, 2024.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/662,700 mailed Jan. 30, 2023.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Corrected Notice of Allowability for U.S. Appl. No. 17/330,657 mailed Dec. 9, 2021.
Corrected Notice of Allowability for U.S. Appl. No. 17/657,474 mailed Mar. 13, 2024.
Final Office Action for U.S. Appl. No. 16/245,726 mailed Nov. 25, 2022.
Final Office Action for U.S. Appl. No. 16/369,676 mailed Aug. 31, 2023.
Final Office Action for U.S. Appl. No. 16/369,676 mailed Dec. 5, 2022.
Final Office Action for U.S. Appl. No. 16/433,773 mailed Oct. 10, 2023.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/449,039 mailed Nov. 21, 2023.
Final Office Action for U.S. Appl. No. 16/452,145 mailed Mar. 25, 2022.
Final Office Action for U.S. Appl. No. 16/452,258 mailed Dec. 21, 2023.
Final Office Action for U.S. Appl. No. 16/452,258 mailed Jun. 14, 2022.
Final Office Action for U.S. Appl. No. 16/478,180 mailed Feb. 28, 2024.
Final Office Action for U.S. Appl. No. 16/478,180 mailed Jun. 22, 2022.
Final Office Action for U.S. Appl. No. 16/478,180 mailed May 31, 2023.
Final Office Action for U.S. Appl. No. 16/904,868 mailed Mar. 10, 2022.
Final Office Action for U.S. Appl. No. 16/904,868 mailed Nov. 2, 2023.
Final Office Action for U.S. Appl. No. 16/905,400 mailed Dec. 9, 2021.
Final Office Action for U.S. Appl. No. 17/051,399 mailed Jan. 8, 2024.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/179,116 mailed Oct. 31, 2023.
Final Office Action for U.S. Appl. No. 17/444,792 mailed Apr. 3, 2024.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/446,654 mailed Jan. 31, 2024.
Final Office Action for U.S. Appl. No. 17/448,811 mailed Aug. 3, 2023.
Final Office Action for U.S. Appl. No. 17/450,864 mailed Dec. 28, 2023.
Final Office Action for U.S. Appl. No. 17/451,345 mailed May 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/645,821 mailed Apr. 3, 2024.
Final Office Action for U.S. Appl. No. 17/646,771 mailed Dec. 21, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/662,700 mailed Sep. 30, 2022.
Final Office Action for U.S. Appl. No. 17/663,330 mailed Dec. 12, 2023.
Final Office Action for U.S. Appl. No. 17/664,487 mailed Jan. 4, 2024.

(56) References Cited

OTHER PUBLICATIONS

Final Office Action for U.S. Appl. No. 17/808,354 mailed Apr. 10, 2024.
Final Office Action for U.S. Appl. No. 18/139,523 mailed Dec. 22, 2023.
Final Office Action for U.S. Appl. No. 18/140,163 mailed Mar. 27, 2024.
Final Office Action for U.S. Appl. No. 18/140,751 mailed Jan. 17, 2024.
Final Office Action for U.S. Appl. No. 18/164,800 mailed Dec. 6, 2023.
International Search Report and Written Opinion from International Application No. PCT/IB2021/057173 mailed Nov. 5, 2021.
International Search Report and Written Opinion from International Application No. PCT/US2020/057562 mailed Jan. 27, 2021.
International Search Report and Written Opinion from International Application No. PCT/US2021/015024 mailed May 18, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/039866 mailed Oct. 7, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044107 mailed Dec. 23, 2022.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.

(56) References Cited

OTHER PUBLICATIONS

International Search Report and Written Opinion from International Application No. PCT/US2023/024805 mailed Dec. 14, 2023.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
Issue Notification for U.S. Appl. No. 16/245,726 mailed Oct. 18, 2023.
Issue Notification for U.S. Appl. No. 16/899,956 mailed Mar. 29, 2023.
Issue Notification for U.S. Appl. No. 16/905,400 mailed Nov. 30, 2022.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/088,272 mailed Jun. 15, 2022.
Issue Notification for U.S. Appl. No. 17/330,657 mailed Jun. 22, 2022.
Issue Notification for U.S. Appl. No. 17/461,036 mailed Oct. 11, 2023.
Issue Notification for U.S. Appl. No. 17/663,046 mailed Dec. 20, 2023.
Issue Notification for U.S. Appl. No. 18/299,788 mailed Feb. 21, 2024.
Non-Final Office Action for U.S. Appl. No. 16/245,726 mailed Jan. 21, 2022.
Non-Final Office Action for U.S. Appl. No. 16/369,676 mailed Feb. 29, 2024.
Non-Final Office Action for U.S. Appl. No. 16/369,676 mailed Mar. 31, 2022.
Non-Final Office Action for U.S. Appl. No. 16/433,773 mailed Apr. 11, 2023.
Non-Final Office Action for U.S. Appl. No. 16/433,773 mailed Apr. 21, 2022.
Non-Final Office Action for U.S. Appl. No. 16/433,773 mailed Feb. 26, 2024.
Non-Final Office Action for U.S. Appl. No. 16/449,039 mailed Apr. 27, 2023.
Non-Final Office Action for U.S. Appl. No. 16/449,039 mailed Dec. 8, 2021.
Non-Final Office Action for U.S. Appl. No. 16/452,145 mailed Mar. 28, 2023.
Non-Final Office Action for U.S. Appl. No. 16/452,145 mailed Nov. 2, 2023.
Non-Final Office Action for U.S. Appl. No. 16/452,145 mailed Sep. 28, 2021.
Non-Final Office Action for U.S. Appl. No. 16/452,258 mailed Apr. 26, 2023.
Non-Final Office Action for U.S. Appl. No. 16/452,258 mailed Sep. 28, 2021.
Non-Final Office Action for U.S. Appl. No. 16/478,180 mailed Dec. 20, 2022.
Non-Final Office Action for U.S. Appl. No. 16/478,180 mailed Nov. 7, 2023.
Non-Final Office Action for U.S. Appl. No. 16/478,180 mailed Oct. 22, 2021.
Non-Final Office Action for U.S. Appl. No. 16/904,868 mailed Mar. 12, 2024.
Non-Final Office Action for U.S. Appl. No. 16/904,868 mailed Mar. 15, 2023.
Non-Final Office Action for U.S. Appl. No. 16/904,868 mailed Oct. 5, 2021.
Non-Final Office Action for U.S. Appl. No. 16/905,400 mailed Apr. 27, 2022.
Non-Final Office Action for U.S. Appl. No. 17/051,399 mailed Aug. 18, 2023.
Non-Final Office Action for U.S. Appl. No. 17/051,550 mailed Dec. 15, 2022.
Non-Final Office Action for U.S. Appl. No. 17/051,550 mailed Oct. 24, 2023.
Non-Final Office Action for U.S. Appl. No. 17/051,585 mailed Jan. 8, 2024.
Non-Final Office Action for U.S. Appl. No. 17/051,585 mailed Mar. 29, 2023.
Non-Final Office Action for U.S. Appl. No. 17/051,600 mailed Jan. 17, 2024.
Non-Final Office Action for U.S. Appl. No. 17/179,116 mailed Feb. 26, 2024.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/330,657 mailed Aug. 11, 2021.
Non-Final Office Action for U.S. Appl. No. 17/444,792 mailed Feb. 10, 2023.
Non-Final Office Action for U.S. Appl. No. 17/444,792 mailed Nov. 17, 2023.
Non-Final Office Action for U.S. Appl. No. 17/446,256 mailed Apr. 13, 2023.
Non-Final Office Action for U.S. Appl. No. 17/446,256 mailed Feb. 13, 2024.
Non-Final Office Action for U.S. Appl. No. 17/446,654 mailed Sep. 8, 2023.
Non-Final Office Action for U.S. Appl. No. 17/448,811 mailed Jan. 17, 2024.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,345 mailed Dec. 7, 2022.
Non-Final Office Action for U.S. Appl. No. 17/451,345 mailed Jan. 17, 2024.
Non-Final Office Action for U.S. Appl. No. 17/451,354 mailed Apr. 4, 2024.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/453,560 mailed Oct. 16, 2023.
Non-Final Office Action for U.S. Appl. No. 17/501,591 mailed Apr. 25, 2023.
Non-Final Office Action for U.S. Appl. No. 17/597,673 mailed Mar. 20, 2024.
Non-Final Office Action for U.S. Appl. No. 17/645,821 mailed Oct. 25, 2023.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/653,137 mailed Jan. 18, 2024.
Non-Final Office Action for U.S. Appl. No. 17/653,920 mailed Mar. 15, 2024.
Non-Final Office Action for U.S. Appl. No. 17/655,464 mailed Mar. 14, 2023.
Non-Final Office Action for U.S. Appl. No. 17/655,464 mailed Mar. 26, 2024.
Non-Final Office Action for U.S. Appl. No. 17/657,474 mailed Sep. 12, 2023.

(56) References Cited

OTHER PUBLICATIONS

Non-Final Office Action for U.S. Appl. No. 17/661,090 mailed Jul. 6, 2023.
Non-Final Office Action for U.S. Appl. No. 17/662,700 mailed Jul. 22, 2022.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 17/664,914 mailed Jan. 31, 2024.
Non-Final Office Action for U.S. Appl. No. 17/808,354 mailed Nov. 28, 2023.
Non-Final Office Action for U.S. Appl. No. 18/003,029 mailed Mar. 26, 2024.
Non-Final Office Action for U.S. Appl. No. 18/134,857 mailed Jan. 25, 2024.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Sep. 14, 2023.
Non-Final Office Action for U.S. Appl. No. 18/164,800 mailed Mar. 22, 2024.
Non-Final Office Action for U.S. Appl. No. 18/198,464 mailed Dec. 7, 2023.
Non-Final Office Action for U.S. Appl. No. 29/741,751 mailed Jan. 18, 2022.
Notice of Allowance for U.S. Appl. No. 16/245,726 mailed Jul. 6, 2023.
Notice of Allowance for U.S. Appl. No. 16/369,676 mailed Nov. 14, 2023.
Notice of Allowance for U.S. Appl. No. 16/449,039 mailed Dec. 15, 2022.
Notice of Allowance for U.S. Appl. No. 16/449,039 mailed Mar. 28, 2024.
Notice of Allowance for U.S. Appl. No. 16/899,956 mailed Apr. 19, 2022.
Notice of Allowance for U.S. Appl. No. 16/899,956 mailed Aug. 10, 2022.
Notice of Allowance for U.S. Appl. No. 16/899,956 mailed Dec. 1, 2022.
Notice of Allowance for U.S. Appl. No. 16/899,956 mailed Dec. 29, 2021.
Notice of Allowance for U.S. Appl. No. 16/905,400 mailed Aug. 17, 2022.
Notice of Allowance for U.S. Appl. No. 17/051,550 mailed Feb. 7, 2024.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/326,980 mailed Apr. 5, 2024.
Notice of Allowance for U.S. Appl. No. 17/326,980 mailed Jan. 29, 2024.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/461,036 mailed Oct. 6, 2022.
Notice of Allowance for U.S. Appl. No. 17/657,474 mailed Mar. 5, 2024.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 17/662,700 mailed Mar. 6, 2024.
Notice of Allowance for U.S. Appl. No. 17/662,700 mailed Nov. 15, 2023.
Notice of Allowance for U.S. Appl. No. 17/663,046 mailed Jan. 30, 2023.
Notice of Allowance for U.S. Appl. No. 18/299,788 mailed Jul. 24, 2023.
Notice of Allowance for U.S. Appl. No. 18/299,788 mailed Nov. 6, 2023.
Notice of Allowance for U.S. Appl. No. 29/741,751 mailed Jun. 9, 2022.
Restriction Requirement for U.S. Appl. No. 16/433,773 mailed Dec. 7, 2021.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Restriction Requirement for U.S. Appl. No. 17/667,097 mailed Mar. 20, 2024.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
Text Messages to Lorena Eckert Re Prototype PureWick Holder dated Apr. 16, 2022.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/384,196, filed Dec. 19, 2016.
U.S. Appl. No. 16/245,726, filed Jan. 11, 2019.
U.S. Appl. No. 17/394,055, filed Aug. 4, 2021.
U.S. Appl. No. 17/444,792, filed Aug. 10, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/451,719, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.

(56) References Cited

OTHER PUBLICATIONS

U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,487, filed May 23, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/249,577, filed Oct. 19, 2021.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/294,370, filed Feb. 1, 2024.
U.S. Appl. No. 18/294,403, filed Feb. 1, 2024.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/610,523, filed Mar. 20, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/485,578, filed Apr. 14, 2017.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 63/008,112, filed Apr. 10, 2020.
U.S. Appl. No. 63/047,374, filed Jul. 2, 2020.
U.S. Appl. No. 63/073,553, filed Sep. 2, 2020.
U.S. Appl. No. 63/094,646, filed Oct. 21, 2020.
U.S. Appl. No. 63/109,084, filed Nov. 3, 2020.
U.S. Appl. No. 63/133,892, filed Jan. 5, 2021.
U.S. Appl. No. 63/138,878, filed Jan. 19, 2021.
U.S. Appl. No. 63/150,640, filed Feb. 18, 2021.
U.S. Appl. No. 63/159,186, filed Mar. 10, 2021.
U.S. Appl. No. 63/191,558, filed May 21, 2021.
U.S. Appl. No. 63/192,289, filed May 24, 2021.
U.S. Appl. No. 63/193,891, filed May 27, 2021.
U.S. Appl. No. 63/208,262, filed Jun. 8, 2021.
U.S. Appl. No. 63/215,017, filed Jun. 25, 2021.
U.S. Appl. No. 63/228,244, filed Aug. 2, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,328, filed Sep. 7, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
U.S. Appl. No. 63/308,190, filed Feb. 9, 2022.
U.S. Appl. No. 63/561,893, filed Dec. 11, 2023.
U.S. Appl. No. 63/596,012, filed Nov. 3, 2023.
U.S. Appl. No. 63/608,553, filed Dec. 11, 2023.
*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
"Rising Warrior Insulated Gallon Jug Cover", https://www.amazon.com/Rising-Warrior-Insulated-Sleeve, 2021, 2 pages.

(56) References Cited

OTHER PUBLICATIONS

"Urine Bag Cover—Catheter Bag Cover 2000 ml Volume—Medline Style—Multiple Sclerosis—Spine Injury—Suprapublic Catheter—Bladder Incontinence", https://www.etsy.com/listing/1142934658/urine-bag-cover-caatheter-bag-cover-2000, 2022, 1 page.

"Vinyl Dust Cover, Janome #741811000, Janome, Sewing Parts Online", https://www.sewingpartsonline.com/vinyl-dust-cover-janome-74181000, 2020, 2 pages.

Ali, "Sustainability Assessment: Seventh Generation Diapers versus gDiapers", The University of Vermont, Dec. 6, 2011, pp. 1-31.

Autumn, et al., "Frictional adhesion: a new angle on gecko attachment", The Journal of Experimental Biology, 2006, pp. 3569-3579.

Cañas, et al., "Effect of nano- and micro-roughness on adhesion of bioinspired micropatterned surfaces", Acta Biomaterialia 8, 2012, pp. 282-288.

Chaudhary, et al., "Bioinspired dry adhesive: Poly(dimethylsiloxane) grafted with poly(2-ethylhexyl acrylate) brushes", European Polymer Journal, 2015, pp. 432-440.

Dai, et al., "Non-sticky and Non-slippery Biomimetic Patterned Surfaces", Journal of Bionic Engineering, Mar. 2020, pp. 326-334.

Espinoza-Ramirez, "Nanobiodiversity and Biomimetic Adhesives Development: From Nature to Production and Application", Journal of Biomaterials and Nanobiotechnology, pp. 78-101, 2019.

Hwang, et al., "Multifunctional Smart Skin Adhesive Patches for Advanced Health Care", Adv. Healthcare Mater, 2018, pp. 1-20.

Jagota, et al., "Adhesion, friction, and compliance of bio-mimetic and bio-inspired structured interfaces", Materials Science and Engineering, 2011, pp. 253-292.

Jeong, et al., "A nontransferring dry adhesive with hierarchical polymer nanohairs", PNAS, Apr. 7, 2009, pp. 5639-5644.

Jeong, et al., "Nanohairs and nanotubes: Efficient structural elements for gecko-inspired artificial dry adhesives", Science Direct, 2009, pp. 335-346.

Karp, et al., "Dry solution to a sticky problem", Nature., 2011, pp. 42-43.

Lee, et al., "Continuous Fabrication of Wide-Tip Microstructures for Bio-Inspired Dry Adhesives via Tip Inking Process", Journal of Chemistry, Jan. 2, 2019, pp. 1-5.

Merriam-Webster Dictionary, "Embed Definition & Meaning", https://www.merriam-webster.com/dictionary/embed last accessed Aug. 3, 2023, 2003.

Parness, et al., "A microfabricated wedge-shaped adhesive array displaying gecko-like dynamic adhesion, directionality", J.R. Soc. Interface, 2009, pp. 1223-1232.

Pieper, et al., "An external urine-collection device for women: A clinical trial", Journal of ER Nursing, vol. 20, No. 2, Mar./Apr. 1993, pp. 51-55.

Tsipenyuk, et al., "Use of biomimetic hexagonal surface texture in friction against lubricated skin", Journal of The Royal Society—Interface, 2014, pp. 1-6.

Vinas, "A Solution For An Awkward—But Serious—Subject", http://www.aero-news.net/index.cfm?do=main.textpost&id=69ae2bb1-838b-4098-a7b5-7flbb2505688 last accessed Feb. 8, 2021.

Wikipedia Article, "Decibel", https://web.archive.org/web/20200415219177/https://en.wikipedia.org/wiki/Decibel last accessed Mar. 11, 2024, 21 pages.

Wikipedia Article, "Fiberglass", https://web.archive.org/web/20200309194847/https://en.wikipedia.org/wiki/Fiberglass last accessed Mar. 11, 2024.

Wikipedia Article, "Zylinder (Geometrie)", https://de.wikipedia.org/w/index.php?title=Zylinder_(Geometrie)&oldid=154862081, version of Jun. 1, 2016, 7 pages.

* cited by examiner

FLUID COLLECTION ASSEMBLIES INCLUDING AT LEAST ONE INFLATION DEVICE

CROSS-REFERENCE TO RELATED APPLICATIONS

This application claims priority to U.S. Provisional Patent Application No. 63/076,474 filed on Sep. 10, 2020, the disclosure of which is incorporated herein, in its entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experience by pilots, drivers, and workers in hazardous areas. Additionally, fluid collection from the individual may be needed for monitoring purposes or clinical testing.

Bed pans and urinary catheters, such as a Foley catheter, may be used to address some of these circumstances. However, bed pans and urinary catheters have several problems associated therewith. For example, bed pans may be prone to discomfort, spills, and other hygiene issues. Urinary catheters be may be uncomfortable, painful, and may cause urinary tract infections.

Thus, users and manufacturers of fluid collection devices continue to seek new and improved devices, systems, and methods to collect urine.

SUMMARY

Embodiments disclosed herein are directed to fluid collection assemblies, systems including the same, and methods of using the same are disclosed herein. In an embodiment, a fluid collection assembly is disclosed. The fluid collection assembly includes a fluid impermeable barrier defining a chamber, at least one opening, and at least one fluid outlet. The fluid impermeable barrier includes at least one proximal surface defining the at least one opening and at least one distal surface opposite the proximal surface. The fluid collection assembly also includes at least one porous material disposed in the chamber. The fluid collection assembly includes at least one inflation device that includes a bladder. The bladder is operably coupled to the fluid impermeable barrier. The bladder includes one or more walls defining at least one interior region, The bladder is configured to switch between a first state and at least a second state. A volume of the at least one interior region is greater when the bladder is in the second state than when the bladder is in the first state. Switching the bladder between the first state and the second state changes a curvature of at least a portion of the fluid impermeable barrier.

In an embodiment, a system is disclosed. The system includes a fluid collection assembly, a fluid storage container, and a vacuum source. the chamber of the fluid collection assembly, the fluid storage container, and the vacuum source are in fluid communication with each other via one or more conduits.

In an embodiment, a method of using a fluid collection assembly is disclosed. The method includes positioning at least one opening of the fluid collection assembly adjacent to a female urethral opening. The fluid collection assembly includes a fluid impermeable barrier defining a chamber, at least one opening, and at least one fluid outlet. The fluid impermeable barrier includes at least one proximal surface defining the at least one opening and at least one distal surface opposite the proximal surface. The fluid collection assembly also includes at least one porous material disposed in the chamber. The fluid collection assembly further includes at least one inflation device including a bladder and at least one valve. The bladder includes one or more walls defining at least one interior region. The method further includes flowing at least one inflation fluid through the at least one valve and into the at least one interior region of the at least one inflation device to change a curvature of the fluid impermeably barrier.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1A:
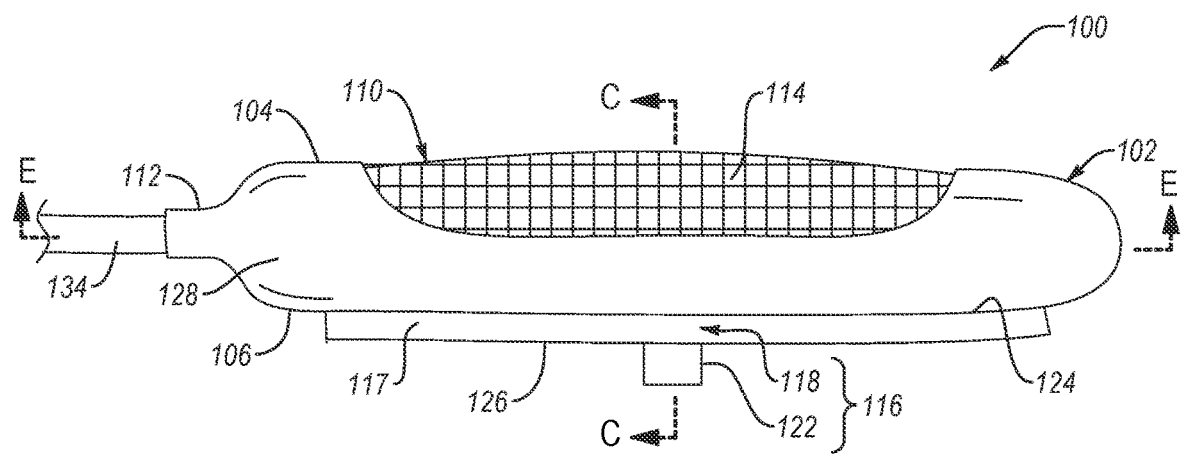
FIGS. 1A and 1B are isometric views of a fluid collection assembly when a bladder of the fluid collection assembly is in a first state and a second state, respectively, according to an embodiment.

Embodiments are directed to fluid collection assemblies, systems including the same, and methods of using the same are disclosed herein. An example fluid collection assembly includes a fluid impermeable barrier having at least one proximal surface configured to be adjacent to an patient (i.e., an individual using the fluid collection assembly) when the fluid collection assembly is in use and at least one distal surface opposite the proximal surface. The fluid impermeable barrier at least defines a chamber, at least one opening defined by the proximal surface, and at least one fluid outlet. The fluid collection assembly also includes at least one porous material disposed in the chamber and at least one inflation device. The inflation device includes a bladder. The bladder may be adjacent to the distal surface of the fluid impermeable barrier or between a conduit disposed in the chamber and the distal surface. The bladder is configured to switch between a first state and at least a second state. A volume of the bladder is greater when the bladder is the second state than when the bladder is in the first state. Switching the bladder between the first state and the second state changes a curvature of at least a portion of the fluid impermeable barrier.

During use, the fluid collection assembly is positioned adjacent to a urethral opening (e.g., vagina) of the patient. One or more bodily fluids (e.g., urine, blood, etc.) that are discharged from the urethral opening of the patient flow through the opening and into the chamber. The bodily fluids that enter the chamber are received into the porous material and are directed towards the fluid outlet. The bodily fluids may be removed from the chamber through the fluid outlet, for example, when a suction force from a vacuum source is applied to the fluid outlet.

Generally, the fluid collection assembly conforms to the shape of the region about the urethral opening to prevent gaps between the fluid collection assembly and the region about the urethral opening. For example, bodily fluids may leak (e.g., do not enter the chamber and/or do not remain in the chamber) through gaps between the fluid collection assembly and the region about the patient. Such leaks may be embarrassing to the patient using the fluid collection assembly, create unsanitary situations, and cause the skin of the patient to remain moist which may cause skin degradation (e.g., rash) and general discomfort.

The region of the patient about the urethral opening may vary in size and shape depending on the patient. Some conventional fluid collection assemblies are manually bent to conform to the shape of the region about the urethral opening to prevent gaps between the conventional fluid collection assemblies and the region about the patient. Contact between the thighs of the patient and the conventional fluid collection assemblies maintains the bent shape of the conventional fluid collection assemblies. However, skinny patients may have too small of thighs to maintain contact with the conventional fluid collection assemblies while forgetful patients (e.g., confused patients, young children, patients with dementia) may move their legs such that the thighs no longer contact the conventional fluid collection assemblies, either of which may cause the fluid collection assembly to loss the bent shape thereof.

Embodiments of the fluid collection assemblies disclosed herein are an improvement to such fluid collection assemblies. As previously discussed, the fluid collection assemblies disclosed herein include at least one inflation device. The inflation device is configured to control the curvature of at least a portion of the fluid impermeable barrier such that the fluid impermeable barrier generally conforms to the shape (e.g., curvature) of the region about the urethral opening. In other words, the inflation device allows the fluid collection assembly to maintain the shape thereof without relying on contact between the fluid collection assembly and the thighs of the patient. As such, the inflation device may minimize gaps between the fluid impermeable barrier and the region about the urethral opening through which bodily fluids may leak. For example, the inflation device includes a bladder that is configured to switch between a first state and at least a second state. The bladder switches from the first state to the second state by increasing a volume thereof and from the second state to the first state by decreasing the volume thereof. The bladder may increase and decrease the volume thereof by adding or removing, respectively, at least one inflation fluid (e.g., air, water, saline, or other suitable fluid) from the bladder. A curvature of the inflation device may change when switching the bladder between the first and second states thereof. For example, the bladder may exhibit a first shape (e.g., first curvature) when the bladder is in the first state and a second shape (e.g., second curvature) when the bladder is in the second state, wherein the first shape and the second shape are different. The shape of at least a portion of the rest of the fluid collection assembly (e.g., fluid impermeable barrier) generally corresponds to the shape of the bladder and, thus, the inflation device may control the shape of the fluid impermeable barrier.

Figure 1B:
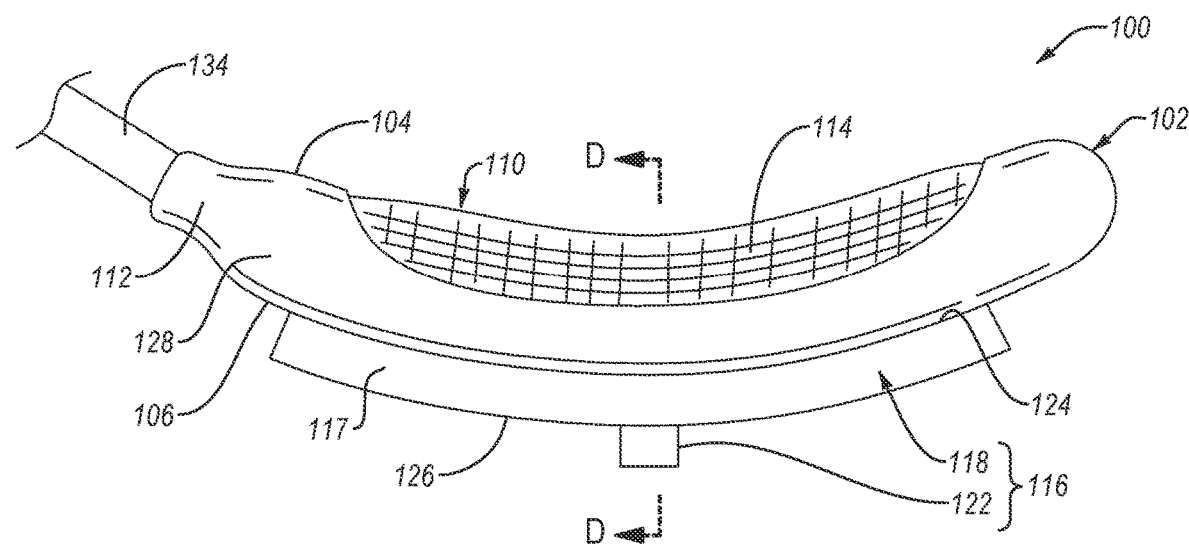
Figure 1C:
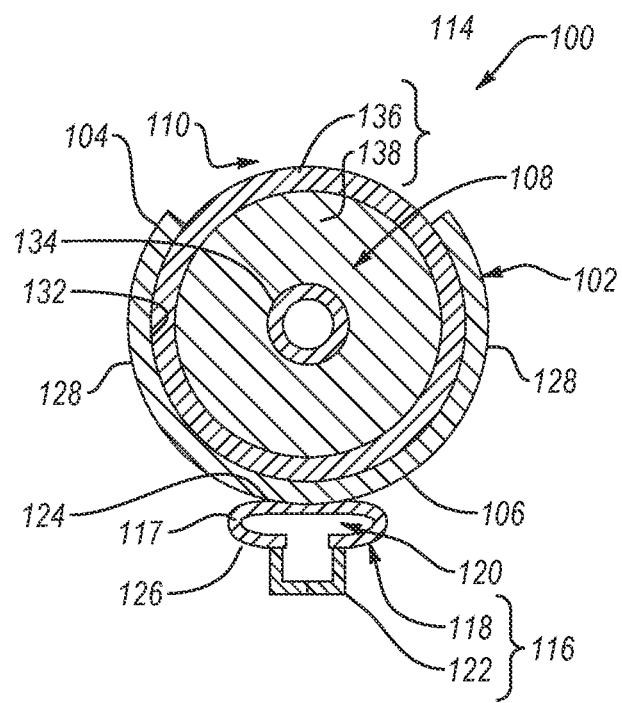
FIGS. 1C and 1D are cross-sectional schematics of the fluid collection assembly taken along planes C-C and D-D shown in FIGS. 1A and 1B, respectively, according to an embodiment.
Figure 1D:
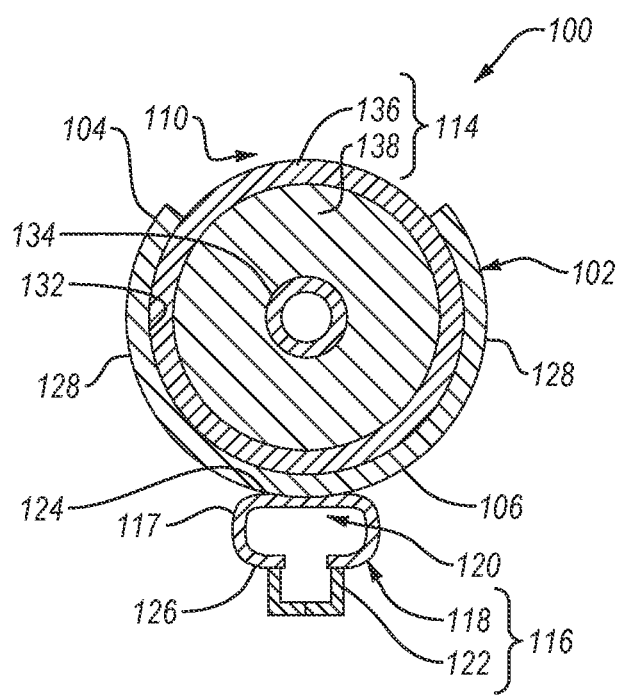
Figure 1E:
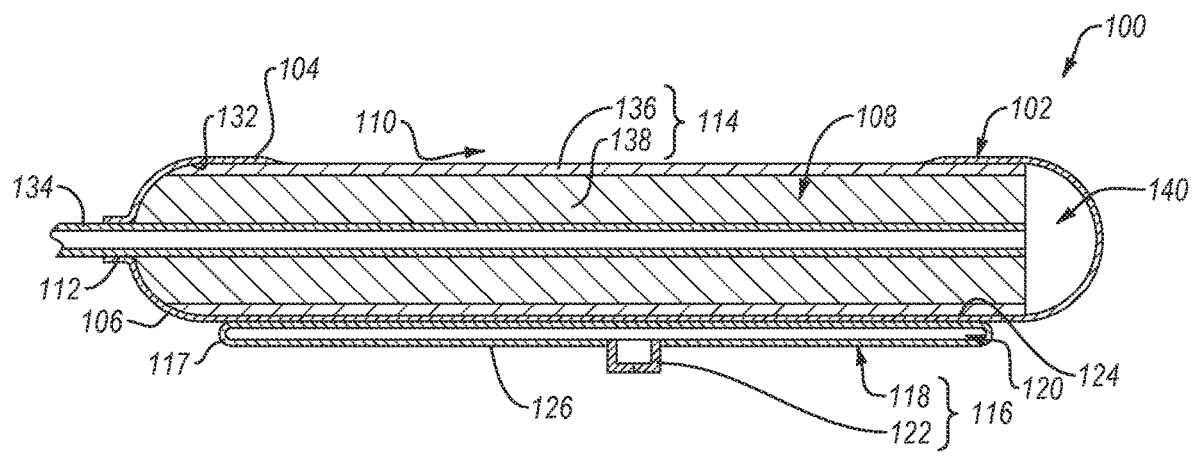
FIG. 1E is a cross-sectional schematic of the fluid collection assembly taken along plane E-E shown in FIG. 1A, according to an embodiment.

FIGS. 1A and 1B are isometric views of a fluid collection assembly 100 when a bladder 118 of the fluid collection assembly 100 is in a first state and a second state, respectively, according to an embodiment. FIGS. 1C and 1D are cross-sectional schematics of the fluid collection assembly 100 taken along planes C-C and D-D shown in FIGS. 1A and 1B, respectively, according to an embodiment. FIG. 1E is a cross-sectional schematic of the fluid collection assembly 100 taken along plane E-E shown in FIG. 1A, according to an embodiment. The fluid collection assembly 100 includes a fluid impermeable barrier 102. The fluid impermeable barrier 102 includes a proximal surface 104 that is configured to be positioned adjacent to an patient during use and a distal surface 106 opposite the proximal surface 104. The fluid impermeable barrier 102 defines at least a chamber 108, at least one opening 110 that is defined by the proximal surface 104, and at least one fluid outlet 112. The fluid collection assembly 100 also includes at least one porous material 114 disposed in the chamber 108 and at least one inflation device 116 adjacent to the distal surface 106.

The inflation device 116 includes a bladder 118. The bladder 118 includes one or more walls 117 defining an interior region 120. The inflation device 116 also includes at least one valve 122 in fluid communication with the interior region 120. The valve 122 is configured to selectively permit flow of an inflation fluid into and/or out of the interior region 120. For example, the valve 122 may allow an inflation fluid to enter the interior region 120 when it is desirable to increase the volume of the bladder 118 which, in turn, changes a shape (e.g., curvature) of the bladder 118 and at least a portion of the fluid impermeable barrier 102. The valve 122 may also enable removing the inflation fluid from the interior region 120 when it is desirable to decrease the volume of the bladder 118 which, in turn changes a shape (e.g., return to the initial shape) of the bladder 118 and at least a portion of the fluid impermeable barrier 102.

Adding or removing the inflation fluids into and from the interior region 120 changes the state of the bladder 118. The bladder 118 may exhibit at least a first state and a second state. The amount (volume or weight) of inflation fluids present in the interior region 120 is greater when the bladder 118 is in the second state than when the bladder 118 is in the first state. In an example, as shown in FIG. 1C, the bladder 118 is in the first state when the bladder 118 is in a deflated state (e.g., there are not or substantially no fluids in the interior region 120). However, it is noted that the bladder 118 may be in the first state when some inflation fluids are present in the interior region 120. Generally, the fluid collection assembly 100 is provided without any inflation fluids in the interior region 120 (e.g., the fluid collection assembly 100 is provided with the bladder 118 in the deflated state) thereby preventing the bladder 118 from leaking during shipping and handling and inhibiting contaminant growth (e.g., bacteria growth) in the interior region 120 before use. In an example, as shown in FIG. 1D, the bladder 118 is in the second state when the bladder 118 is in an at least partially inflated state. The fluid collection assembly 100 is generally not provided with the bladder 118 in the second state since the inflation fluids may leak during shipping and handling and the inflation fluids may encourage contaminant growth more than if the bladder 118 was provided in an deflated state. However, in some examples, the fluid collection assembly 100 is provided in the second state.

The bladder 118 may exhibit one or more additional states (e.g., a third state, a fourth state, and so forth) besides the first and second states discussed above. In an embodiment, the one or more additional states may include less inflation fluids in the interior region 120 (e.g., is more deflated) than the first state (e.g., the first state is a partially inflated state). In such an embodiment, the one or more additional states may include a deflated or partially deflated state and may be formed by removing inflation fluids from the interior region 120 when the bladder 118 is in the first or second state. In an embodiment, the one or more additional states may include more inflation fluids in the interior region 120 (e.g., is more inflated) than the first state (e.g., the first state is a deflated or partially inflated state) and include less inflation fluids in the interior region 120 than the second state. In such an embodiment, the one or more additional states include a partially inflated state and may be formed by adding or removing inflation fluids to the interior region 120 when the bladder 118 is in the first state or second state, respectively. In an embodiment, the one or more additional states may include more inflation fluids in the interior region 120 than the second state (e.g., the second state is a partially inflated state). In such an embodiment, the one or more additional states may be an at least partially inflated state and may be formed by adding inflation fluids to the interior region 120 when the bladder 118 is in the first state or second state. It is noted that, in some embodiments, the bladder 118 may only include the first and second states.

As shown in FIGS. 1A and 1B, switching the bladder 118 between the first state and the second state (or any of the other states thereof) changes the shape of the bladder 118. As discussed herein, changing the shape of the bladder 118 generally refers to changing at least a curvature of the bladder 118. Changing the shape of the bladder 118 causes at least a portion of the rest of the fluid collection assembly 100, such as at least a portion of the fluid impermeable barrier 102, to change a shape thereof that generally corresponds to the shape of the bladder 118. In an embodiment, as illustrated, the bladder 118 may exhibit a generally straight shape (e.g., exhibits a radius of curvature greater than about 25 cm) when the bladder 118 is in a first state (e.g., deflated state). In such an embodiment, at least a portion of the rest of the fluid collection assembly 100 may exhibit a generally straight shape when the bladder 118 is in the first state. The bladder 118 and the fluid collection assembly 100 may exhibit the generally straight shape when the bladder 118 is in the first state, for example, when the fluid collection assembly 100 would exhibit the substantially straight shape when the inflation device 116 is omitted from the fluid collection assembly 100. For instance, the bladder 118 may be flimsy or flexible and exert substantially no force on the rest of the fluid collection assembly 100 that is sufficient to significantly modify a shape of the rest of the fluid collection assembly 100 when the bladder 118 is in the first state. Switching the bladder 118 from the first state to the second state may cause the bladder 118 to exhibit a generally curved shape (e.g., exhibits an average radius of curvature less than about 40 cm, such as less than about 35 cm, less than about 30 cm, less than about 25 cm, less than about 20 cm, less than about 15 cm, or less than about 10 cm). The curved shape of the bladder 118 may be a concave curved shape relative to the opening 110. Similarly, at least a portion of the fluid collection assembly 100 may exhibit a generally curved shape when the bladder 118 is in the second state. For example, inflating the bladder 118 may increase the rigidity of the bladder 118 such that the bladder 118 exerts a force on the rest of the fluid collection assembly 100 that is sufficient to change a shape of the rest of the fluid collection assembly 100. The radius of curvature of the bladder 118 and the fluid collection assembly 100 may be controlled based on the amount of bodily fluids that are present in the interior region 120. For example, increasing the amount of inflation fluids in the interior region 120 may decrease the average radius of curvature of the bladder 118 and the fluid collection assembly 100. Similarly, decreasing the amount of inflation fluids in the interior region 120 may increase the radius of curvature of the bladder 118. Thus, the amount of inflation fluids in the interior region 120 may control the shape of the fluid collection assembly 100 and may be used to shape the fluid collection assembly 100 to exhibit a shape that corresponds to the shape of the region about the urethral opening.

In an embodiment, not shown, the bladder 118 and the fluid collection assembly 100 may exhibit a curved shape (e.g., a radius of curvature less than about 40 cm, less than about 25 cm, etc.) when the bladder 118 is in the first state. The curved shape of the bladder 118 may be a concave curve relative to the opening 110. The bladder 118 and the fluid collection assembly 100 may exhibit the curved shape when the bladder 118 is in the first state, for example, when the fluid collection assembly 100 would exhibit the curved shape when the inflation device 116 is omitted from the fluid collection assembly 100. For instance, the bladder 118 may be flimsy and exert no force on the rest of the fluid collection assembly 100 that is sufficient to significantly modify a shape of the rest of the fluid collection assembly 100 when the bladder 118 is in the first (e.g., deflated) state. Switching the bladder 118 to the second state may either increase or decrease the radius of curvature of the bladder 118 depending on the shape that the bladder assumes when inflated. Similarly, switching the bladder 118 to the second state may either increase or decrease the average radius of curvature of the rest of the fluid collection assembly 100. Thus, the amount of inflation fluids in the interior region 120 may control the shape of the fluid collection assembly 100 and may be used to shape the fluid collection assembly 100 to exhibit a shape that corresponds to the shape of the region about the urethral opening.

The shape that the bladder 118 assumes when switching the bladder 118 from the first state to the second state may be controlled by configuring different portions of the bladder 118 to expand at different rates (hereafter referred to as "expansion rate"). The expansion rate may be determined by taking the absolute value of the length of at least a portion (e.g., all) of bladder 118 when the bladder 118 is in the first state minus the length of the same portion of the bladder 118 when the bladder 118 is in the second state, wherein the length is measured parallel to the longitudinal axis of the fluid collection assembly 100. In an embodiment, the walls 117 of the bladder 118 includes a first region 124 and a second region 126 opposite the first region 124. The first region 124 and the second region 126 generally face the same direction as the proximal surface 104 and the distal surface 106, respectively. The first region 124 and the second region 126 may exhibit different expansion rates. In an embodiment, as illustrated, the first region 124 exhibits an expansion rate that is less than the second region 126. As such, switching the bladder 118 from the first state to the second state causes a decrease an average radius of curvature of the bladder 118 (i.e., causes the bladder 118 to bend) because a length of the second region 126 increases more than a length of the first region 124 when the bladder 118 switches from the first state to the second state. In an embodiment, the first region 124 exhibits an expansion rate that is greater than the second region 126. FIGS. 2-6 illustrate some examples of techniques that may be used to cause the first region 124 to exhibit different expansion rates than the second region 126.

The shape (e.g., curvature) that the bladder 118 assumes when in the first state, second state, and, optionally, the one or more additional states depend on a number of factors. For example, the shape that the bladder 118 assumes when the bladder 118 is in a deflated (e.g., first) state may be dictated by the shape of the rest of the fluid collection assembly 100. For instance, the bladder 118 may be formed from a relatively flexible material which allows the bladder 118 to be inflated. However, without any inflation fluids in the interior region 120, the bladder 118 merely conforms to the shape of the fluid collection assembly 100. Increasing the quantity of the inflation fluids in the interior region 120 to or near a level where the inflation fluids cause the bladder 118 to stretch may increase the rigidity of the bladder 118 to the point that the bladder 118 may exhibit a shape that is different than the fluid collection assembly 100. The shape that the bladder 118 exhibits may be, for example, an arc (e.g., a portion of a circle, oval, or other curve), one or more bends between adjacent straight or curved portions, or any other suitable shape. The different shapes that the bladder 118 may exhibit may be controlled by selecting the expansion rates of at least one of the first and second regions 124, 126, different portions of the first region 124 (e.g., one portion of the first region 124 may exhibit an expansion rate that is different than another portion of the first region 124), or different portions of the second region 126 (e.g., one portion of the second region 126 may exhibit an expansion rate that is different than another portion of the second region 126). In an example, the bladder 118 may exhibit a generally circular arc in the second state when substantially all the first region 124 exhibits the substantially same expansion rate and substantially all of the second region 126 exhibits the substantially same expansion rate, wherein the expansion rates of the first and second regions 124, 126 are different. In an example, the bladder 118 may exhibit a generally oval arc, other arc, or a bend therein when a portion of the first region 124 exhibits a different expansion rate than another portion of the first region 124 and/or when a portion of the second region 126 exhibits a different expansion rate than another portion of the second region 126. The expansion rates of the first and second regions 124, 126 may be selected based on factors discussed in more detail with regards to FIGS. 2-6.

In an embodiment, as illustrated, the inflation device 116 is positioned such that the first region 124 is adjacent to the distal surface 106 of the fluid impermeable barrier 102. Positioning the first region 124 adjacent to the distal surface 106 allows the inflation device 116 to change the shape of at least a portion of the rest of the rest of the fluid collection assembly 100. Further, a width of the bladder 118 (e.g., measured perpendicular to a length of the bladder 118 and perpendicular to thickness measured between the first and second regions 124, 126) may increase when the bladder 118 switches from the first state to the second state. However, positioning the first region 124 adjacent to the distal surface 106 may prevent the increase in the width of the bladder 118 from increasing the maximum width of the fluid collection assembly 100 when the bladder 118 switches from the first state to the second state, wherein the width of the fluid collection assembly 100 is measured perpendicular to the width of the bladder 118. The maximum width of the fluid collection assembly 100 does not change when the bladder 118 switches from the first state to the second state because the width of the bladder 118 is less than the maximum width of the fluid collection assembly 100 and/or the width of the bladder 118 does not need to significantly increase to significantly change the shape of the bladder 118. It is noted that not increasing the maximum width of the fluid collection assembly 100 when switching the bladder 118 from the first state to the second state allows the fluid collection assembly 100 to be used comfortably with patient's having average or larger than average sized thighs. For example, patients having average or larger than average thighs do not have much space between the thighs to accommodate an increased width of the fluid collection assembly 100 without uncomfortably pressing into the thighs.

The fluid impermeable barrier 102 may include at least one lateral surface 128 extending between the proximal and distal surfaces 104, 106. The lateral surface 128 may be adjacent to a thigh of an patient when the fluid collection assembly 100 is worn by the patient. In an embodiment, as discussed, above, the bladder 118 may be positioned adjacent to the distal surface 106 and not adjacent to the lateral surface 128 to prevent the bladder 118 from increasing the maximum width of the fluid collection assembly 100. In an embodiment, the bladder 118 may be positioned adjacent to the lateral surface 128 of the fluid impermeable barrier 102. In such an embodiment, switching the bladder 118 from the first state to the second state may increase the width of the fluid collection assembly 100. Increasing the width of the fluid collection assembly 100 may improve contact between smaller than average thighs and the fluid collection assembly 100. Further, when the bladder 118 is positioned adjacent to the lateral surface 128, the fluid collection assembly 100 may require two inflation devices on opposing sides of the lateral surface 128 and both inflation devices may need to receive the same amount of inflation fluids to ensure that the fluid collection assembly 100 is symmetrically shaped thereby making the manufacturing and use of the inflation device 116 more complex. It is noted that gaps may form between the fluid collection assembly 100 and the patient when the fluid collection assembly 100 is shaped non-symmetrically.

The walls 117 of the bladder 118 are formed from a material is substantially impermeable to the inflation fluid (e.g., substantially impermeable to a gas and/or a liquid) which allows the bladder 118 to retain the inflation fluids without leaks. The walls 117 may also be formed from a flexible material. The flexible material of the walls 117 allows the bladder 118 and, by extension, the fluid collection assembly 100 to change a shape thereof. For example, the flexible material of the walls 117 allow the interior region 120 to increase a volume thereof when the interior region 120 receives an inflation fluid and decrease a volume thereof when inflation fluids are removed from the interior region 120 which, in turn, changes the shape of the bladder 118. Examples of materials that may form the walls 117 of the bladder 118 include silicone, rubber, latex, polychloroprene, nylon fabric, polypropylene, polyvinyl chloride, nitrile rubber, other suitable polymers, a metal foil, a composite, or combinations thereof. It is noted that the walls 117 may contact the patient and might be formed from a biocompatible material. In an embodiment, the walls 117 are configured to stretch (e.g., elastically or plastically stretch) so the walls 117 remain taut when the bladder 118 is at least partially inflated. In an embodiment, the wall 117 forms a plurality of wrinkles when the bladder 118 is at least partially deflated and adding inflation fluid into the interior region 120 decreases the wrinkles.

The valve 122 (illustrated schematically) may include any suitable valve configured to allow for the controllable addition and removal of inflation fluids from the interior region 120. In an embodiment, the valve 122 is a luer valve and includes a male-tapper fitting or a female-taper fitting. In an embodiment, the valve 122 includes a fluid impermeable membrane with a slit or opening formed therein. The slit or opening of the fluid impermeable membrane remains substantially closed when no external load is applied thereto but opens when an external load is applied thereto (e.g., an external load caused by pressing a syringe against the fluid impermeable membrane). In an embodiment, the valve 122 may include a mechanical valve, such as a ball valve, a butterfly valve, or any other suitable mechanical valve. The mechanical valve may be manually operated or controlled using a computer. In an embodiment, the valve 122 may include a one-way valve (e.g., check valve) to limit leaks from the bladder 118 and to make the fluid collection assembly 100 easier to use. In such an embodiment, the valve 122 may only add or remove (but not both) inflation fluid from the interior region 120 and, as such, the fluid collection assembly 100 including the check valve is configured for single use. In an embodiment, the valve 122 may include a two-way valve which allows the inflation fluid to be added and removed from the interior region 120. In such an embodiment, at least a portion of the fluid collection assembly 100 (e.g., the fluid impermeable barrier 102 and the inflation device 116) may be reusable.

In an embodiment, as illustrated, the valve 122 may extend outwardly from the bladder 118. For example, the valve 122 may extend from the bladder 118 thereby allowing a user (e.g., medical practitioner or patient) of the fluid collection assembly 100 to easily access the valve 122. As shown, the valve 122 may extend a short distance only from the fluid impermeable barrier 102, such as about 2 cm or less, about 1.5 cm or less, about 1 cm or less, about 0.75 cm or less, about 0.5 cm or less, about 0.25 cm or less, or in ranges of about 0.25 cm to about 0.75 cm, about 0.5 cm to about 1 cm, about 0.75 cm to about 1.5 cm, or about 1 cm to about 2 cm. However, the valve 122 may extend a significant distance from the fluid impermeable barrier 102, such as a distance that is about 2 cm or greater, about 5 cm or greater, about 10 cm or greater, about 50 cm or greater, about 100 cm or greater, about 500 cm or greater, about 1 m or greater, about 2 m or greater, or in ranges of about 2 cm to about 10 cm, about 5 cm to about 50 cm, about 10 cm to about 100 cm, about 50 cm to about 500 cm, about 100 cm to about 1 m, or about 500 cm to about 2 m. When the valve 122 extends a significant distance from the fluid impermeable barrier 102, the valve 122 may include a flexible tube which allows a user of the fluid collection assembly 100 to easily access to the valve 122 while the fluid collection assembly 100 is positioned adjacent to the urethral opening without having the user near the urethral opening (which the patient may find uncomfortable).

In an embodiment, as illustrated, the valve 122 extends from or near a second region 126 of the bladder 118. The valve 122 at or near the second region 126 may allow a user of the fluid collection assembly 100 to access the valve 122 when the fluid collection assembly 100 is adjacent to the urethral opening since, generally, the inner thighs of the patient may contact or obstruct the proximal and lateral surfaces 104, 128 of the fluid impermeable barrier 102. Further, the valve 122 at or near the second region 126 prevents or at least inhibits the valve 122 from pressing against the inner thighs during use which may cause discomfort.

The at least one inflation fluid added or removed from the interior region 120 may include any suitable fluid, such as any suitable liquid or any suitable gas. In an embodiment, the inflation fluids are formed from a generally regarded as safe ("GRAS") material. Forming the inflation fluids from a GRAS materials may decrease health risks caused by inadvertently exposing the patient to the inflation fluids. Examples of GRAS materials that may form the inflation fluids includes water, saline solution, alcohol solution, atmospheric air, nitrogen, any other GRAS material, or combinations thereof.

Further examples of inflation devices are disclosed in U.S. Provisional Patent Application No. 63/030,685 filed on May 27, 2020, the disclosure of which is incorporated herein, in its entirety, by this reference.

As previously discussed, the fluid collection assembly 100 includes a fluid impermeable barrier 102. In the illustrated embodiment, the fluid impermeable barrier 102 is distinct from the inflation device 116.

The fluid impermeable barrier 102 may be formed of any suitable fluid impermeable material(s), such as a fluid impermeable polymer (e.g., silicone, polypropylene, polyethylene, polyethylene terephthalate, a polycarbonate, etc.), a metal film, natural rubber, another suitable material, or combinations thereof. The fluid impermeable barrier 102 substantially prevents the bodily fluids from passing through the fluid impermeable barrier 102. In an example, the fluid impermeable barrier 102 may be air permeable and fluid impermeable. In such an example, the fluid impermeable barrier 102 may be formed of a hydrophobic material that defines a plurality of pores. At least a surface of the fluid impermeable barrier 102 that may contact the patient may be formed from a soft and/or smooth material (e.g., silicone), thereby reducing chaffing. In an embodiment, the fluid impermeable barrier 102 may be formed from a flexible material, such as silicone, which allows the fluid impermeable barrier 102 to be bent into a shape that conforms the anatomy of the patient. Further, as shown in FIGS. 1B and 1C, forming the fluid impermeable barrier 102 from a flexible material allows the fluid impermeable barrier 102 to accommodate the shape and/or size changes by switching the fluid collection assembly 100 and the bladder 118 between states.

In some examples, the fluid impermeable barrier 102 may be tubular (ignoring the opening), such as substantially cylindrical (as shown), oblong, prismatic, or flattened tubes. During use, the outer surface (e.g., at least a portion of one or more of the proximal surface 104, the distal surface 106, or the lateral surface 128) of the fluid impermeable barrier 102 may contact the patient. The fluid impermeable barrier 102 may be sized and shaped to fit in the gluteal cleft between the legs of a female user when the bladder 118 are in at least the second state.

The opening 110 provides an ingress route for fluids to enter the chamber 108. The opening 110 may be defined by the fluid impermeable barrier 102 such as by an inner edge of the fluid impermeable barrier 102. For example, the opening 110 is formed in and extends through the fluid impermeable barrier 102, from the proximal surface 104 to an inner surface 132 of the fluid impermeable barrier 102, thereby enabling bodily fluids to enter the chamber 108 from outside of the fluid collection assembly 100. The opening 110 may be an elongated hole in the fluid impermeable barrier 102. For example, the opening 110 may be defined as a cut-out in the fluid impermeable barrier 102. The opening 110 may be located and shaped to be positioned adjacent to a female urethral opening.

The fluid collection assembly 100 may be positioned proximate to the female urethral opening and urine or other bodily fluids may enter the chamber of the fluid collection assembly 100 via the opening 110. The fluid collection assembly 100 is configured to receive the bodily fluids into the chamber 108 via the opening 110. When in use, the opening 110 may have an elongated shape that extends from a first location below the urethral opening (e.g., at or near the anus or the vaginal opening) to a second location above the urethral opening (e.g., at or near the top of the vaginal opening or the pubic hair).

The opening 110 may have an elongated shape because the space between the legs of a female is relatively small when the legs of the female are closed, thereby only permitting the flow of the bodily fluids along a path that corresponds to the elongated shape of the opening 110 (e.g., longitudinally extending opening). The opening 110 in the fluid impermeable barrier 102 may exhibit a length measured along the longitudinal axis of the fluid collection assembly 100 that may be at least about 10% of the length of the fluid collection assembly 100, such as about 25% to about 50%, about 40% to about 60%, about 50% to about 75%, about 65% to about 85%, or about 75% to about 95% of the length of the fluid collection assembly 100.

The opening 110 in the fluid impermeable barrier 102 may exhibit a width measured transverse to the longitudinal axis of the fluid collection assembly 100 that may be at least about 10% of the circumference of the fluid collection assembly 100, such as about 25% to about 50%, about 40% to about 60%, about 50% to about 75%, about 65% to about 85%, or about 75% to about 100% of the circumference of the fluid collection assembly 100. The opening 110 may exhibit a width that is greater than 50% of the circumference of the fluid collection assembly 100 since the vacuum (e.g., suction) through the conduit 134 pulls the fluid through the porous material 114 and into the conduit 134.

In some examples, the opening 110 may be vertically oriented (e.g., having a major axis parallel to the longitudinal axis of the fluid collection assembly 100). In some examples (not shown), the opening 110 may be horizontally oriented (e.g., having a major axis perpendicular to the longitudinal axis of the fluid collection assembly 100). In an example, the fluid impermeable barrier 102 may be configured to be attached to the patient, such as adhesively attached (e.g., with a hydrogel adhesive) to the patient. According to an example, a suitable adhesive is a hydrogel layer.

As previously discussed, the fluid impermeable barrier 102 may define fluid outlet 112 configured to remove bodily fluids from the chamber 108. The fluid outlet 112 is distinct from the opening 110 and the valve 122. In some examples, the fluid outlet 112 is sized to receive the conduit 134. The conduit 134 may be disposed in the chamber 108 via the fluid outlet 112. The fluid outlet 112 may be sized and shaped to form an at least substantially fluid tight seal against the conduit 134 or the at least one tube substantially preventing the bodily fluids from escaping the chamber 108.

The fluid impermeable barrier 102 may include markings thereon, such as one or more markings to aid a user in aligning the fluid collection assembly 100 on the patient. For example, a line on the fluid impermeable barrier 102 (e.g., opposite the opening 110) may allow a healthcare professional to align the opening 110 over the urethral opening of the patient. In examples, the markings may include one or more of alignment guide or an orientation indicator, such as a stripe or hashes. Such markings may be positioned to align the fluid collection assembly 100 to one or more anatomical features such as a pubic bone, etc.

As previously discussed, the fluid collection assembly 100 includes porous material 114 disposed in the chamber 108. The porous material 114 may cover at least a portion (e.g., all) of the opening 110. The porous material 114 is exposed to the environment outside of the chamber 108 through the opening 110. The permeable properties referred to herein may be wicking, capillary action, absorption, diffusion, or other similar properties or processes, and are referred to herein as "permeable" and/or "porous." The porous material 114 may also wick the bodily fluids generally towards an interior of the chamber 108, as discussed in more detail below. The porous material 114 may include one or more of a fluid permeable membrane 136 or a fluid permeable support 138.

In an embodiment, at least a portion of the porous material 114 may be a wicking material configured to wick and/or enable the bodily fluids to move away from the opening 110, thereby preventing bodily fluids from escaping the chamber 108. The porous material may not include absorption of the bodily fluids into the porous material. Put another way, substantially no absorption of the bodily fluids into the porous material may take place after the wicking material is exposed to the bodily fluids. While no absorption is desired, the term "substantially no absorption" may allow for nominal amounts of absorption of the bodily fluids into the porous material (e.g., absorbency), such as about 30 wt % of the dry weight of the porous material, about 20 wt %, about 10 wt %, about 7 wt %, about 5 wt %, about 3 wt %, about 2 wt %, about 1 wt %, or about 0.5 wt % of the dry weight of the porous material. In an embodiment, the porous material 114 may be at least one of an absorbent material or adsorbent material instead of or in addition to being a wicking material.

The fluid collection assembly 100 may include the fluid permeable membrane 136 disposed in the chamber 108. The fluid permeable membrane 136 may cover at least a portion (e.g., all) of the opening 110. The fluid permeable membrane 136 may be composed to pull/push the bodily fluids away from the opening 110, thereby promoting fluid flow into the chamber 108, prevent fluid remaining on the vulva of the patient, and preventing the bodily fluids from escaping the chamber 108.

The fluid permeable membrane 136 may include any material that may be permeable to the bodily fluids. For example, the fluid permeable membrane 136 may include fabric, such as a gauze (e.g., a silk, linen, or cotton gauze), another soft fabric, or another smooth fabric. Forming the fluid permeable membrane 136 from gauze, soft fabric, and/or smooth fabric may reduce chaffing caused by the fluid collection assembly 100 and makes wearing the fluid collection assembly more comfortable. In an embodiment, the fluid permeable membrane 136 may define a plurality of perforations or may be continuous (e.g., does not define perforations). In an embodiment, the fluid permeable membrane 136 defines at least one hole that is configured to allow the valve 122 to extend through the fluid permeable membrane 136.

The fluid collection assembly 100 may include the fluid permeable support 138 disposed in the chamber 108. The fluid permeable support 138 is configured to support the fluid permeable membrane 136 and maintain the shape of the chamber 108 since the fluid impermeable barrier 102 and the fluid permeable membrane 136 may be formed from a relatively foldable, flimsy, or otherwise easily deformable material. For example, the fluid permeable support 138 may be positioned so the fluid permeable membrane 136 is disposed between the fluid permeable support 138 and the fluid impermeable barrier 102. The fluid permeable support 138 may support and maintain the position of the fluid permeable membrane 136 and the shape of the chamber 108. The fluid permeable support 138 may include any material that may be permeable to the bodily fluids, such as any of the fluid permeable membrane 136 materials disclosed above. For example, the fluid permeable membrane 136 material(s) may be utilized in a more dense or rigid form than in the fluid permeable membrane 136 when used as the fluid permeable support 138. The fluid permeable support 138 may be formed from any fluid porous material that is less deformable than the fluid permeable membrane 136. For example, the fluid permeable support 138 may include a porous polymer (e.g., nylon, polyester, polyurethane, polyethylene, polypropylene, etc.) structure (e.g., spun fibers such as spun nylon fibers) or a foam (e.g., an open cell foam). In some examples, the fluid permeable support 138 may be formed from a natural material, such as cotton, wool, silk, or combinations thereof. In such examples, the material may have a coating to prevent or limit absorption of the bodily fluids into the material, such as a water repellent coating. In some examples, the fluid permeable support 138 may be formed from fabric, felt, gauze, or combinations thereof.

In some examples, the fluid permeable membrane 136 may be omitted. For example, the porous material 114 may include only the fluid permeable support 138. In such examples, the bladder 118 may be positioned within the fluid permeable support 138 since, for instance, at least some materials of the support 138 disclosed herein are flexible enough to accommodate the shape and/or size changes discussed herein. In some examples, the fluid permeable support 138 may be optionally omitted from the fluid collection assembly 100 and the porous material 114 may only include the fluid permeable membrane 136. In such examples, the bladder 118 may be positioned within the fluid permeable membrane 136.

In an embodiment, the fluid permeable membrane 136 and/or the fluid permeable support 138 are wicking materials. In such an embodiment, the fluid permeable support 138 may have a greater ability to wick the bodily fluids than the fluid permeable membrane 136. In some examples, the wicking ability of the fluid permeable support 138 and the fluid permeable membrane 136 may be substantially the same. In an embodiment, the fluid permeable membrane 136 and/or the fluid permeable support 138 are non-wicking materials (e.g., absorbent and/or adsorbent materials).

In an embodiment, not shown, the fluid permeable membrane 136 and the fluid permeable support 138 may at least substantially completely fill the portions of the chamber 108 not occupied by the inflation device 116 and the conduit 134. In an embodiment, as shown in FIG. 1E, the fluid permeable membrane 136 and the fluid permeable support 138 may not substantially completely fill the portions of the chamber 108 not occupied by the inflation device 116 or the conduit 134. In such an embodiment, the fluid collection assembly 100 includes the fluid reservoir 140 disposed in the chamber 108.

The fluid reservoir 140 is a substantially unoccupied portion of the chamber 108. The fluid reservoir 140 may be defined between the fluid impermeable barrier 102 and at least one of the inflation device 116, the fluid permeable membrane 136, or the fluid permeable support 138. The bodily fluids in the chamber 108 may flow through the fluid permeable membrane 136 and/or fluid permeable support 138 to the fluid reservoir 140. The fluid reservoir 140 may retain of the bodily fluids. The bodily fluids in the chamber 108 may flow through the fluid permeable membrane 136 and/or fluid permeable support 138 and, optionally, to the fluid reservoir 140. The fluid impermeable barrier 102 may retain the bodily fluids in the fluid reservoir 140. The fluid reservoir 140 may be in a portion of the chamber 108 designed to be in a gravimetrically low point of the fluid collection assembly 100 when the fluid collection assembly 100 is worn.

Figure 2:
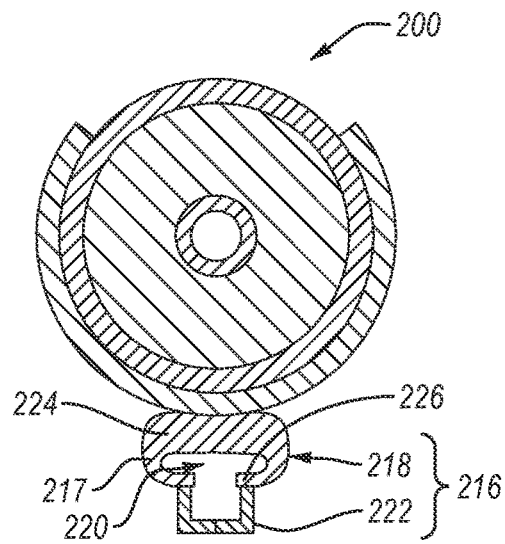
FIGS. 2-4 are cross-sectional schematics and FIGS. 5 and 6 are side views of different fluid collection assemblies illustrating different techniques for controlling the expansion rate of the first and second regions of the bladders, according to different embodiments.
Figure 3:
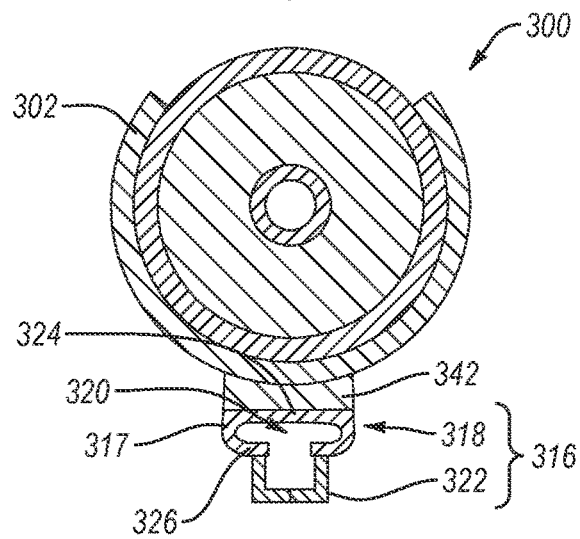
Figure 4:
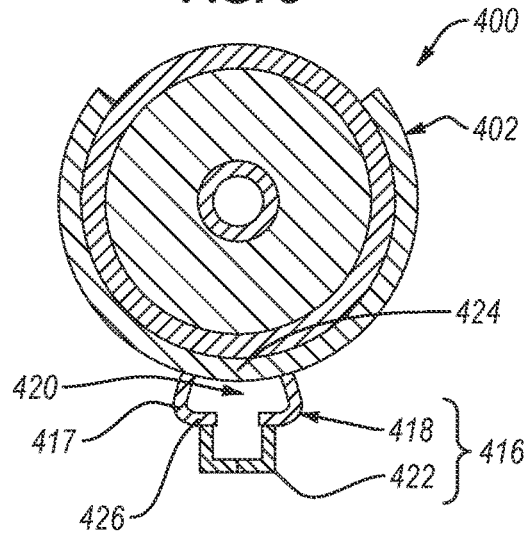
Figure 5:
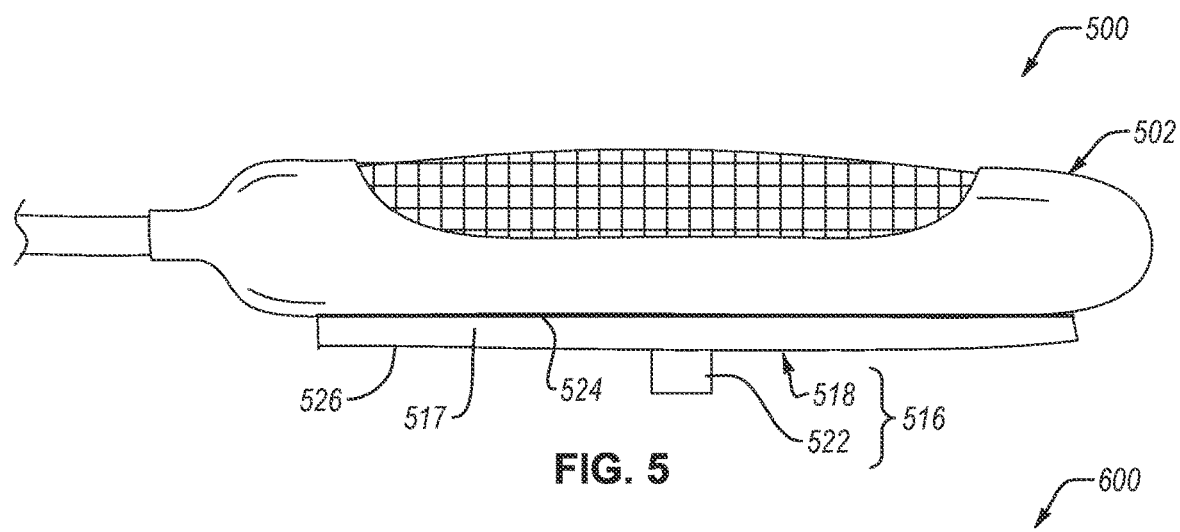
Figure 6:
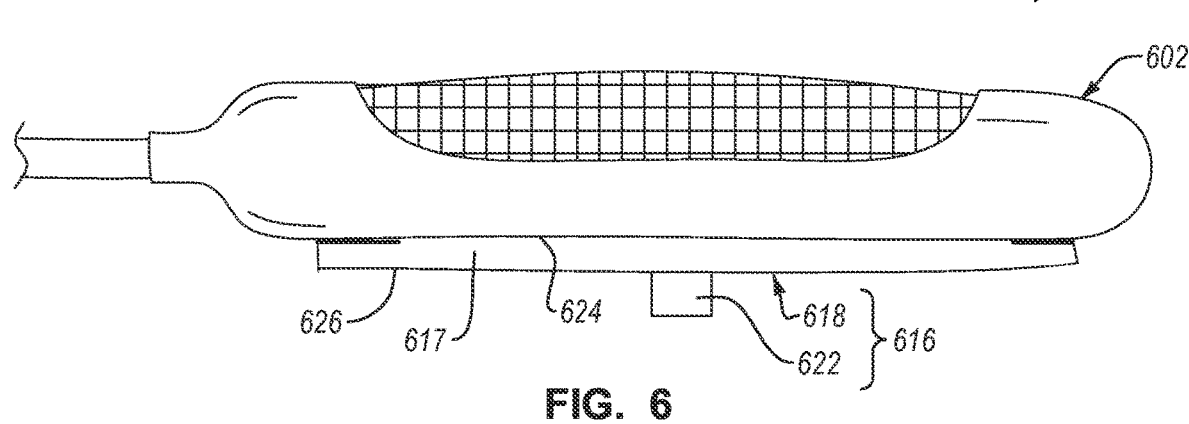

FIGS. 2-4 are cross-sectional schematics and FIGS. 5 and 6 are side views of different fluid collection assemblies illustrating different techniques for controlling the expansion rate of the first and second regions of the bladders, according to different embodiments. Except as otherwise disclosed herein, the fluid collection assemblies illustrated in FIGS. 2-6 are the same or substantially similar to any of the fluid collection assemblies disclosed herein. For example, the fluid collection assemblies illustrated in FIGS. 2-6 may include a fluid impermeable barrier defining at least one opening, a chamber, and a fluid outlet. The fluid collection assemblies also include at least one porous material disposed in the chamber and at least one inflation device. The features of the fluid collection assemblies illustrated in FIGS. 2-6 may also be used in any fluid collection assemblies disclosed herein.

Referring to FIG. 2, the inflation device 216 of the fluid collection assembly 200 includes a bladder 218 and a valve 222. The bladder 218 includes one or more walls 217 defining an interior region 220. The bladder 218 includes a first region 224 and a second region 226. In the illustrated embodiment, the first and second regions 224, 226 are formed from the walls 217. The first region 224 and the second region 226 exhibit different thicknesses. The different thicknesses of the 224, 226 cause the first and second regions 224, 226 to exhibit different expansion rates when the bladder 218 switches from the first state to the second state.

The first region 224 exhibits a first thickness and an opposing portion of the second region 226 exhibits a second thickness that is different than the first thickness. For example, the first thickness may be greater than the second thickness, or vice versa, by at least about 1%, at least about 2%, at least about 3%, at least about 4%, at least about 5%, at least about 7.5%, at least about 10%, at least about 15%, at least about 20%, at least about 25%, at least about 30%, at least about 40%, at least about 50%, at least about 60%, at least about 70%, at least about 80%, at least about 90%, at least about 100%, at least about 125%, at least about 150%, at least about 200%, at least about 250%, at least about 300%, at least about 350%, at least about 400%, at least about 500%, or in ranges of about 1% to about 3%, about 2%, to about 4%, about 3% to about 5%, about 4% to about 7.5%, about 5% to about 10%, about 7.5% to about 15%, about 10% to about 20%, about 15% to about 25%, about 20% to about 40%, about 30% to about 50%, about 40% to about 60%, about 50% to about 70%, about 60% to about 80%, about 70% to about 90%, about 80% to about 100%, about 90% to about 125%, about 100% to about 150%, about 125% to about 200%, about 150% to about 250%, about 200% to about 300%, about 250% to about 350%, about 300% to about 400%, or about 350% to about 500%. As will be discussed in more detail below, the different between the first thickness and the second thickness may be selected based on the desired expansion rates of the opposing portions of the first and second regions 224, 226 which, in turn, affects the shape that the bladder 218 assumes when switching between the first and second states.

In an example, as illustrated, the first thickness is greater than the second thickness. The greater thickness of the first region 224 relative to the second region 226 causes the first region 224 to exhibit a smaller expansion rate than the second region 226. As such, the length of the first region 224 increases less than the length of the second region 226 when the bladder 218 switches from the first state to the second state which causes the bladder 218 to bend towards the first region 224. In other words, if the bladder 218 is initially straight, the increased thickness of the first region 224 causes the bladder 218 to form a curved shape with the first region 224 forming the concaved portion of the curved shape. In an example, the first thickness is less than the second thickness. The smaller thickness of the first region 224 relative to the second region 226 causes the first region 224 to exhibit an expansion rate that is greater than the second region 226. In other words, the length of the first region 224 increases more than the length of the second region 226 when the bladder 218 switches from the first state to the second state which causes the bladder 218 to bend towards the second region 226. In other words, if the bladder 218 is initially curved such that the first region 224 is concavely curved, the decreases thickness of the first region 224 causes the bladder 218 to form a more straight shape.

The shape that the bladder 218 forms when switching the bladder 218 between the first and second states may be controlled at least partially based on the thicknesses of the first and second regions 224, 226. In an embodiment, the bladder 218 may form a generally circular arc when each of the thickness of the first region 224 and the thickness of the second region 226 are substantially constant along the length of the bladder 218. In an embodiment, the thickness of at least one of the first region 224 or the second region 226 may be selectively varied which causes the expansion rate of different portions of the first region 224 and/or the second region 226 to vary. In an example, decreasing the thickness of a portion of the first region 224 relative to another portion of the first region 224 may cause the thinner portion of the first region 224 to exhibit a greater expansion rate than the thicker portion of the first region 224. In such an example, using the illustrated embodiment, the thinner portion of the first region 224 may bend more (e.g., exhibit a smaller average radius of curvature) than the thicker portion of the first region 224. In an example, decreasing the thickness of a portion of the second region 226 relative to another portion of the second region 226 may cause the thinner portion of the second region 226 to exhibit an expansion rate that is greater than the thicker portion of the second region 226.

Referring to FIG. 3, the inflation device 316 of the fluid collection assembly 300 includes a bladder 318 and a valve 322. The bladder 318 includes one or more walls 317 defining an interior region 320. The bladder 318 includes a first region 324 and a second region 326. In the illustrated embodiment, the first and second regions 324, 326 are formed from the walls 317. The inflation device 316 also includes at least one additional layer 342 attached to at least a portion of at least one of the first region 324 or the second region 326. The additional layer 342 is distinct from the walls 317.

The additional layer 342 effectively increases the thickness of the portion of the first region 324 and/or the second region 326 to which the additional layer 342 is adjacent. As such, similar to the different thicknesses discussed with regards to FIG. 2, the additional layer 342 may be used to control the shape that the bladder 318 assumes when switching the bladder 318 between the first and second states. In particular, the increased thickness caused by the additional layer 342 may decrease the expansion rate of the portion(s) of the bladder 318 to which the additional layer 342 is adjacent.

In an embodiment, the additional layer 342 may exhibit a Young's modulus (modulus of elasticity) that is greater than the walls 317 of the bladder 318. The increased Young's modulus of the additional layer 342 allows the additional layer 342 to exhibit the same effect as a thicker region of the walls 317 but at a smaller thickness. As such, the additional layer 342 may decrease the amount that the bladder 318 extends from the fluid impermeable barrier 302 than if bladder 318 included a region with increased thickness. The decreased profile of the bladder 318 may make the bladder 318 more comfortable to wear, especially with larger thighs since there is not significant space between the larger thighs in which to position the fluid collection assembly 300. In an example, the additional layer 342 includes a substantially inflexible fabric. In an example, the additional layer 342 includes a wire, a plate, a substantially inflexible polymer, a metal, or a composite.

The shape that the bladder 318 forms when switching the bladder 318 between the first and second states may be controlled based on which portions of the bladder 318 to which the additional layer 342 is adjacent and the Young's modulus of the additional layer 342. In an embodiment, the bladder 318 may form a generally circular arc when the additional layer 342 is adjacent to one or more of the first region 324 or the second region 326 along an entire length thereof. In an embodiment, the additional layer 342 is selectively positioned adjacent to only a portion of the length of one or more of the first region 324 or the second region 326. The portion(s) of the first region 324 and/or second region 326 to which the additional layer 342 is adjacent may exhibit an expansion rate that is less than portion(s) of the first regions 324 and/or second region 326 that are not spaced from the additional layer 342. In an embodiment, the additional layer 342 may be selectively formed form two or more portions, where at least two of the two or more portions exhibit different Young's moduli. Each of the two or more portions may extend along different lengths of the additional layer 342. For instance, the additional layer 342 may include a first portion exhibiting a first Young's modulus and a second portion exhibiting a second Young's modulus that is greater than the first Young's modulus. In such an instance, the portions of the bladder 318 adjacent to the first portion of the additional layer 342 may exhibit an expansion rate that is greater than the portions of the bladder 318 adjacent to the second portion of the additional layer 342.

Referring to FIG. 4, the inflation device 416 of the fluid collection assembly 400 includes a bladder 418 and a valve 422. The bladder 418 includes one or more walls 417. The walls 417 and a portion of the fluid impermeable barrier 402 defines an interior region 420 of the bladder 418. For example, the bladder 418 includes a first region 424 at least partially formed by the fluid impermeable barrier 402 and a second region 426 formed by the walls 417. The walls 417 may be attached to the fluid impermeable barrier 402 in a fluid tight manner such that inflation fluids present in the interior region 420 do not leak from the interior region 420. Inflating the bladder 418 will cause a tensile force to be applied to the portion of the fluid impermeable barrier 402 that defines the interior region 420, thereby causing the portion of the fluid impermeable barrier 402 that defines the interior region 420 to expand.

The fluid impermeable barrier 402 may exhibit an expansion rate that is different than the walls 417. In an example, the fluid impermeable barrier 402 may exhibit an expansion rate that is less than the walls 417. The fluid impermeable barrier 402 may exhibit the lower expansion rate because at least one of the fluid impermeable barrier 402 is thicker than the walls 417, the fluid impermeable barrier 402 exhibits a Young's modulus that is greater than the walls 417, or the portions of the fluid impermeable barrier 402 that do not define the interior region 420 apply a force to the first region 424 that limits expansion of the portions of the fluid impermeable barrier 402 that define the interior region 420. In an example, the fluid impermeable barrier 402 may exhibit an expansion rate that is greater than the walls 417. In such an example, the fluid impermeable barrier 402 may exhibit the larger expansion rate because at least one of the fluid impermeable barrier 402 is thinner than the walls 417 or the fluid impermeable barrier 402 exhibits a Young's modulus that is less than the walls 417.

Referring to FIG. 5, the fluid collection assembly 500 includes a fluid impermeable barrier 502 and at least one inflation device 516. The inflation device 516 includes a bladder 518 and at least one valve 522. The bladder 518 includes one or more walls 517 that completely define an interior region (not shown, obscured). The one or more walls 517 are attached to the fluid impermeable barrier 502 along substantially an entire length of the bladder 518 (attachment is illustrated schematically with a bold line). For example, as illustrated, the bladder 518 includes a first region 524 and a second region 526 and at least substantially all of the first region 524 is attached to the fluid impermeable barrier 502. Attaching substantially an entire length of the bladder 518 effectively increases the thickness of the portion of the bladder 518 that is attached to the fluid impermeable barrier 502. In other words, the fluid impermeable barrier 502 decreases the expansion rate of a surface of the bladder 518 that is attached to the fluid impermeable barrier 502 than if the portion of the bladder 518 was not attached to the fluid impermeable barrier 502.

The bladder 518 may be attached to the fluid impermeable barrier 502 using any suitable technique. For example, the bladder 518 may be attached to the fluid impermeable barrier 502 using an adhesive, radio frequency welding, ultrasonic welding, tape (e.g., double sided tape positioned between bladder 518 and the fluid impermeable barrier 502 or tape that wraps around at least a portion of the bladder 518 and is attached to the fluid impermeable barrier 502), or any other suitable attachment technique.

Referring to FIG. 6, the fluid collection assembly 600 includes a fluid impermeable barrier 602 and at least one inflation device 616. The inflation device 616 includes a bladder 618 and at least one valve 622. The bladder 618 includes one or more walls 617 that completely define an interior region (not shown, obscured). The one or more walls 617 are attached to the fluid impermeable barrier 602 along a portion of the length of the bladder 618 (attachment is illustrated schematically with a bold line). For example, the bladder 618 may include a first region 624 adjacent to the fluid impermeable barrier 602 and a second region 626 spaced from the first region 624. In such an example, the expansion rate of at least the first region 624 of the portion of the bladder 618 that is attached to the fluid impermeable barrier 602 is limited because the fluid impermeable barrier 602 effectively increases the thickness of such portions of the first region 624.

In an embodiment, two or more portions of the bladder 618 are attached to the fluid impermeable barrier 602. For example, as illustrated, two or more portions of the bladder 618 at or near the terminal ends of the bladder 618 are attached to the fluid impermeable barrier 602. The expansion rate of a surface of the bladder 618 that is adjacent to the fluid impermeable barrier 602 (i.e., the first portion 624) and is between two or more portions of the bladder 618 that are attached to the fluid impermeable barrier 602 is limited because the two or more portions that are attached to the bladder 618 exhibits a compressive force that limit the expansion rate. In other words, the surface of the bladder 618 that is adjacent to the fluid impermeable barrier 602 and is between two or more portions of the bladder 618 exhibits an expansion rate that is less than an opposing portion of the bladder 618.

Figure 7:
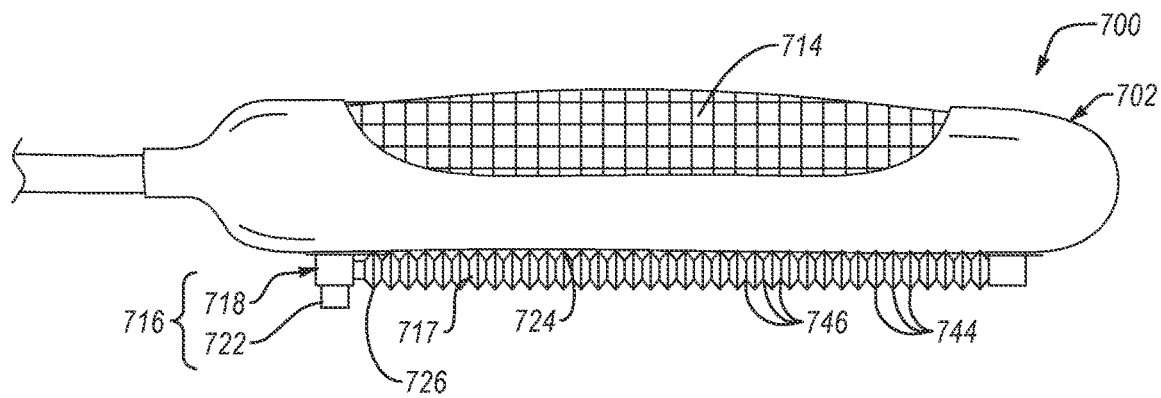
FIG. 7 is side view of a fluid collection assembly that includes a "crinkle" shaped bladder, according to an embodiment.

The embodiments illustrated and discussed in FIGS. 1A-6 include a bladder that exhibits a substantially uniform diameter. However, it is noted that any of the bladders disclosed herein may exhibit other shapes. For example, FIG. 7 is side view of a fluid collection assembly 700 that includes a "crinkle" or bellows shaped bladder 718, according to an embodiment. Except as otherwise disclosed herein, the fluid collection assembly 700 is the same or substantially similar to any of the fluid collection assemblies disclosed herein. For example, the fluid collection assembly 700 includes a fluid impermeable barrier 702, at least one porous material 714, and at least one inflation device 716.

The inflation device 716 includes a bladder 718 and at least one valve 722. The bladder 718 includes one or more walls 717 defining an interior region (not shown, obscured). The bladder 718 exhibits a "crinkle" structure (i.e., the bladder 718 is a crinkle shaped bladder). For example, the bladder 718 may include one or more peaks 744 (e.g., a plurality of circumferentially extending peaks 744 or a single helically extending peak 744). The bladder 718 also includes one or more valleys 746 (e.g., a plurality of circumferentially extending valleys 746 or a single helically extending valley 746) disposed between portions of the peaks 744 space apart along a longitudinal direction of the bladder 718. The peaks 744 and the valleys 746 allow the bladder 718 to bend when switching the bladder 718 from the first state to the second state. For example, adding inflation fluids to the bladder 718 may cause the distance between the peaks 744 on the second region 726 to increase while the distance between the peaks 744 on the first region 724 may decrease, remain constant, or increase at a rate that is less than the second region 726.

The inflation device 716 may be attached to the fluid impermeable barrier 702 using any suitable technique (e.g., adhesive, tape, ultrasonic welding, etc.) along at least a portion of a length thereof. In an example, only the terminal ends of the inflation device 716 (e.g., the terminal ends may not include the "crinkle structure") may be attached to the fluid impermeable barrier 702. In an example, some or all of the peaks 744 may be attached to the fluid impermeable barrier 702. In an example, some or all of the valleys 746 may be attached to the fluid impermeable barrier 702. In an example, two or more of the terminal ends, at least some of the peaks 744, or at least some of the valleys 746 of the inflation device 716 are attached to the fluid impermeable barrier 702.

Figure 8:
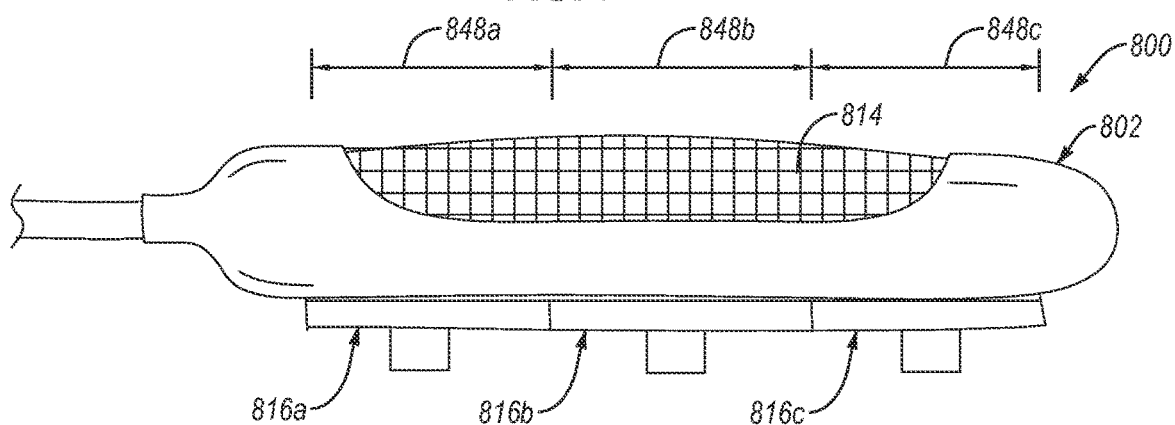
FIG. 8 is a side view of a fluid collection assembly that includes a plurality of inflation devices, according to an embodiment.

The embodiments illustrated in FIGS. 1A-7 illustrate that the fluid collection assemblies include a single inflation device. However, any of the fluid collection assemblies may include a plurality of inflation devices. FIG. 8 is a side view of a fluid collection assembly 800 that includes a plurality of inflation devices, according to an embodiment. Except as otherwise disclosed herein, the fluid collection assembly 800 may be the same or substantially similar to any of the fluid collection assemblies disclosed herein. For example, the fluid collection assembly 800 includes a fluid impermeable barrier 402 and at least one porous material 814.

As previously discussed, the fluid collection assembly 800 includes a plurality of inflation devices that may be independently inflated and/or deflated. For example, as illustrated, the fluid collection assembly includes a first inflation device 816a, a second inflation device 816b, and a third inflation device 816c. Each of the first inflation device 816a, the second inflation device 816b, and the third inflation device 816c may be the same or substantially similar to any of the inflation devices disclosed herein. For example, each of the first inflation device 816a, the second inflation device 816b, and the third inflation device 816c may a bladder having one or more walls defining and interior region and at least one valve. In an example, each of the first, second, and third inflation devices 816a, 816b, 816c are the same. In an example, at least two of the first, second, and third inflation devices 816a, 816b, 816c are different (e.g., exhibit different lengths, exhibit different expansion rates, limit the expansion rates thereof using different techniques, etc.).

Each of the first, second, and third inflation devices 816a, 816b, 816c are configured to control the shape of a corresponding portion of the fluid impermeable barrier 802. For example, the first inflation device 816a may be configured to control the shape of a first portion 848a of the fluid collection assembly 800, the second inflation device 816b may be configured to control the shape of a second portion 848b of the fluid collection assembly 800, and the third inflation device 816c may be configured to control the shape of a third portion 848c of the fluid collection assembly 800. As such, the first, second, and third inflation devices 816a, 816b, 816c allow for more control of the shape of the fluid collection assembly 800 that if the fluid collection assembly 800 included a single inflation device. In an example, one or two of the first, second, or third inflation devices 816a, 816b, 816c may be switched from the first state to the second state while the remainder of the first, second, or third inflation devices 816a, 816b, 816c remain in the first state. The inflation device(s) that are switched to the second state cause the corresponding portions of the fluid collection assembly to change shape while the inflation device(s) that remain in the first state cause the corresponding portions of the fluid collection assembly to remain in the original shape thereof. In an example, each of the first, second, or third inflation devices 816a, 816b, 816c are switched from the first state to the second state. In such an example, one or two of the first, second, or third inflation devices 816a, 816b, 816c may include changing (e.g., reducing) an average radius of curvature of a corresponding portion of the fluid collection assembly 800 more than the remaining one or two of the first, second, or third inflation devices 816a, 816b, 816c.

In an embodiment, the fluid collection assembly 800 may include two inflation devices or four or more inflation devices. In other words, the third inflation device 816c may be omitted from the fluid collection assembly 800 or the fluid collection assembly 800 may include one or more additional inflation devices in addition to the first, second, and third inflation devices 816a, 816b, 816c. In an embodiment, as shown, the first, second, and third portions 848a, 848b, 848c of the fluid impermeable barrier 802 may not overlap. However, it is noted that two or more of the first, second, or third portions 848a, 848b, 848c may overlap such that a shape of such overlapped portions may be controlled by two different inflation devices.

Figure 9:
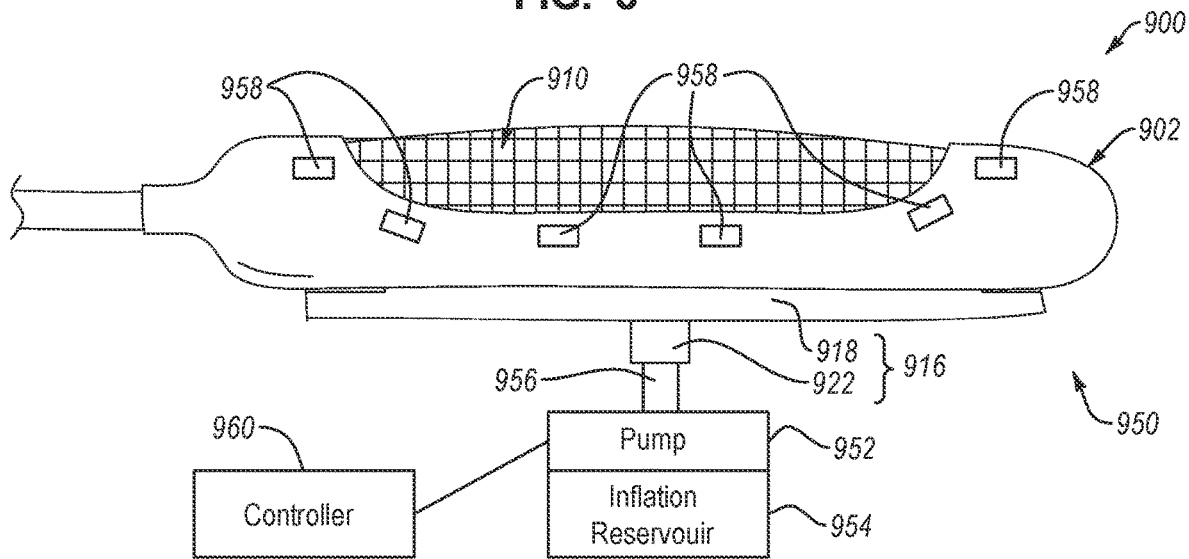
FIG. 9 is a schematic side view of a fluid collection system that is configured to control the shape of a fluid collection assembly, according to an embodiment.

FIG. 9 is a schematic side view of a fluid collection system 950 that is configured to control the shape of a fluid collection assembly 900, according to an embodiment. The system 950 includes a fluid collection assembly 900. Except as otherwise disclosed herein, the fluid collection assembly 900 is the same or substantially similar to any of the fluid collection assemblies disclosed herein. For example, the fluid collection assembly 900 may include a fluid impermeable barrier 902 and at least one inflation device 916. The inflation device 916 includes a bladder 918 defining an interior region (not shown, obscured) and a valve 922.

The system 950 also includes at least one pump 952 and at least one inflation fluid reservoir 954 configured to store one or more inflation fluids therein. The inflation fluid reservoir 954 may include a tank that stores the inflation fluids therein or may be the atmosphere (e.g., the inflation fluids are atmospheric air). The pump 952 and the inflation fluid reservoir 954 are in fluid communication to the inflation device 916 via at least one conduit 956. For example, the conduit 956 may extend from the pump 952 and/or the inflation fluid reservoir 954 to a valve 922 of the inflation device 916. In an embodiment, the pump 952 may be configured to provide the inflation fluids to the inflation device 916 from the inflation fluid reservoir 954. The inflation fluids provided to the inflation device 916 may flow through the valve 922 into the interior region defined by the bladder 918 to switch the bladder 918 from the first state to the second state. As such, the pump 952 and the inflation fluid reservoir 954 may change the shape of the fluid collection assembly 900 from a first (e.g., initial) shape to a second shape. In an embodiment, the pump 952 and the inflation fluid reservoir 954 may be configured to remove the inflation fluids from the inflation device 916 instead of or in addition to providing the inflation fluids to the inflation device 916. In such an embodiment, the pump 952 may provide a suction force that removes at least some of the inflation fluids from the interior region of the bladder 918 which switches the bladder 918 from the second state to the first state. Switching the bladder 918 from the second state to the first state may change the fluid collection assembly 900 from the second shape to the first state. The inflation fluids removed from the interior region of the bladder may be deposited in the inflation fluid reservoir 954.

In an embodiment, the system 950 may be controlled responsive to receiving input from a user of the system 950 (e.g., a medical practitioner or a patient). The input may include verbal commands, manipulating one or more actuators (e.g., buttons, levers, etc.), or one or more electronic instructions sent from a computer. The pump 952 and the inflation fluid reservoir 954 may provide and/or remove inflation fluids from the inflation device 916 responsive to receiving the one or more inputs. In an embodiment, the system 950 may be at least partially controlled without receiving one or more inputs from the user of the system 950. In such an embodiment, the system 950 may include one or more sensor 958 that are configured to detect contact between a portion of the fluid collection assembly 900 and the patient. For example, the sensors 958 may include an array of contact sensors arranged around the opening 910 which allows the sensors 958 to detect whether one or more gaps are formed between the portions of the fluid impermeable barrier 902 that define the opening 910. The sensors 958 may be communicably coupled to a controller 960 (e.g., computer) and configured to transmit one or more signals to the control electric circuitry 960. The signals transmitted from the sensors 958 to the control electric circuitry 960 may include the characteristics detected by the sensors 958. The control electric circuitry 960 may control the pump 952 responsive to receiving the one or more signals from the sensors 958. For example, the control electric circuitry 960 may cause the pump 952 to add or remove inflation fluids from the inflation device 916 when the sensor 958 indicate that there are gaps between the fluid impermeable barrier 902 and the patient.

Figure 10:
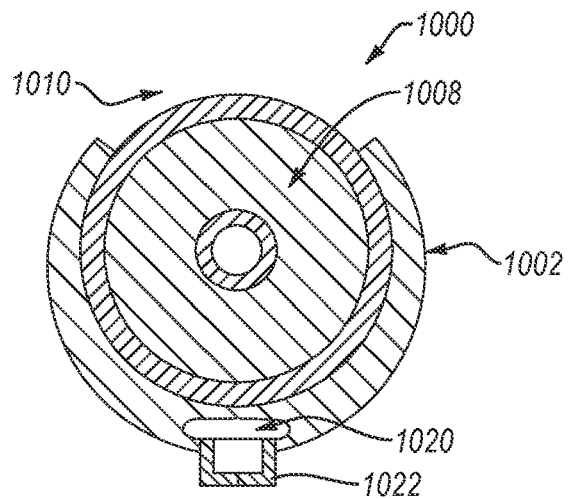
FIGS. 10-12 are cross-sectional schematics of fluid collection assemblies having at least one inflation device positioned at locations other than an outer surface of the fluid impermeable barrier, according to different embodiments.
Figure 11:
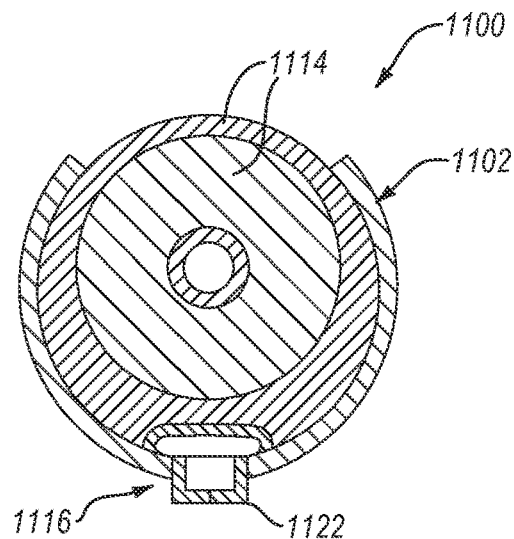
Figure 12:
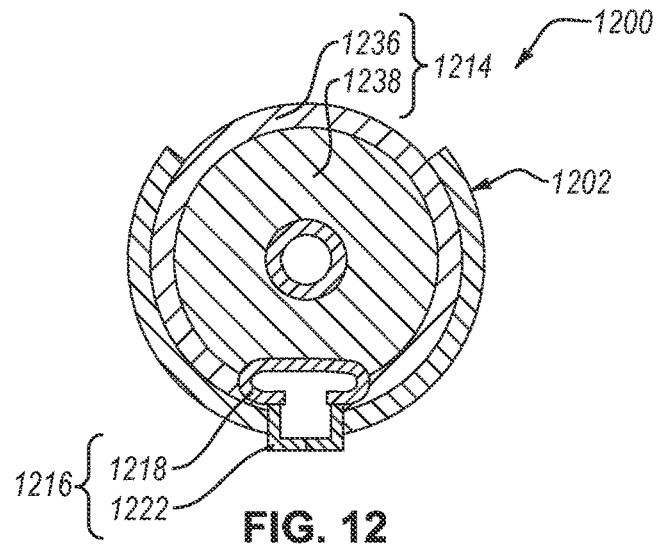

The embodiments illustrated in FIGS. 1A-9 illustrate the inflation device being disposed on an outer surface of the fluid impermeable barrier. However, it is noted that the inflation devices of any of the fluid collection assemblies disclosed herein may be positioned at locations other than the outer surface of the fluid impermeable barrier. FIGS. 10-12 are cross-sectional schematics of fluid collection assemblies having at least one inflation device positioned at locations other than an outer surface of the fluid impermeable barrier, according to different embodiments. Except as otherwise disclosed herein, the fluid collection assemblies illustrated in FIGS. 10-12 are the same or substantially similar to any of the fluid collection assemblies disclosed herein. For example, the fluid collection assemblies may each include a fluid impermeable barrier, at least one porous material, at least one inflation device, and a conduit. The inflation device may include a bladder and at least one valve. The bladder may include one or more walls at least partially defining an interior region. It is noted that the bladders are generally illustrated as being generally positioned between the conduit and a distal surface of the fluid impermeable barrier thereby minimizing the likelihood that switching the bladder from the first state to the second state significantly increases a maximum width of the fluid collection assembly for reasons previously discussed. However, it is noted that the bladders may be positioned between the conduit and a lateral surface of the fluid impermeable barrier.

Referring to FIG. 10, the fluid collection assembly 1000 includes a fluid impermeable barrier 1002. The fluid impermeable barrier 1002 forms the at least a portion of the inflation device (e.g., the fluid impermeable barrier 1002 and at least a portion of an inflation device are integrally formed together). The impermeable barrier 1002 may exhibit any of the properties and functions as any of the fluid impermeable barriers and inflation devices disclosed herein. For example, the impermeable barrier 1002 may define a chamber 1008, at least one opening 1010, and a fluid outlet and may be configured to prevent bodily fluids from leaking from the chamber 1008. The impermeable barrier 1002 may also include a bladder defining an interior region 1020. The impermeable barrier 1002 is configured to switch between one or more states (e.g., a first state and a second state) by adding or removing inflation fluids to the interior region 220 using a valve 1022.

Referring to FIG. 11, the fluid collection assembly 1100 includes a fluid impermeable barrier 1102 and at least one porous material 1114. The fluid collection assembly 1100 also includes at least one inflation device 1116 that is distinct from the fluid impermeable barrier 1102. At least a portion of the inflation device 1116 (e.g., at least the bladder 1118) is positioned between the fluid impermeable barrier 1102 and the porous material 1114. The fluid impermeable barrier 1102 may protect the inflation device 1116 from objects that may puncture the inflation device 1116. The fluid impermeable barrier 1102 may define an aperture through which the valve 1122 may extend. The aperture may be configured to form a fluid tight seal against the valve 1122 to prevent leaks between the aperture and the valve 1122.

Referring to FIG. 12, the fluid collection assembly 1200 includes a fluid impermeable barrier 1202 and at least one porous material 1214. The fluid collection assembly 1200 also include at least one inflation device 1216. At least a portion of the inflation device 1216 (e.g., at least the bladder 1218) is positioned within the porous material 1214. For example, when the porous material 1214 includes a fluid permeable membrane 1236 and a fluid permeable support 1238, at least a portion of the inflation device 1216 may be disposed between the fluid permeable membrane 1236 and the fluid permeable support 1238. As such, the fluid impermeable barrier 1202 and at least a portion of the porous material 1214 may protect the inflation device 1216 from objects that may puncture the inflation device 1216. The fluid impermeable barrier 1202 and at least a portion of the porous material 1214 may define an aperture through which the valve 1222 may extend. The aperture may be configured to form a fluid tight seal against the valve 1222 to prevent leaks between the aperture and the valve 1222.

It is noted that the inflation devices disclosed herein may have positions other that the positions illustrated in FIGS. 1A-12. For example, the inflation devices may be positioned within the fluid permeable membrane, within the fluid permeable support, between the fluid permeable support and the conduit, within the conduit, or integrally formed with the conduit.

In an embodiment, the conduit of any of the fluid collection assemblies disclosed herein (e.g., conduit 134 of FIGS. 1A-1E) may exhibit an initial shape when the conduit is in its relaxed state. The conduit is in its relaxed state when no external forces, such as forces caused by an inflation device (e.g., the inflation device is in a deflated state), are applied to the conduit. The initial shape of the conduit may be a generally cylindrical shape (e.g., the conduit is straight) or a slightly curved generally cylindrical shape. Changing the shape of the inflation device, such as switching the bladder of the inflation device from the first state to the second state, may apply an external force to the conduit that causes the conduit to change the shape thereof. However, the conduit may resist changing the shape thereof when the external force are applied to the conduit which causes the conduit to apply a normal force that is opposite the external force. The normal force from the conduit may cause the conduit to compress a portion of the porous material and/or may cause the formation of detrimental voids in the chamber.

Figure 13A:
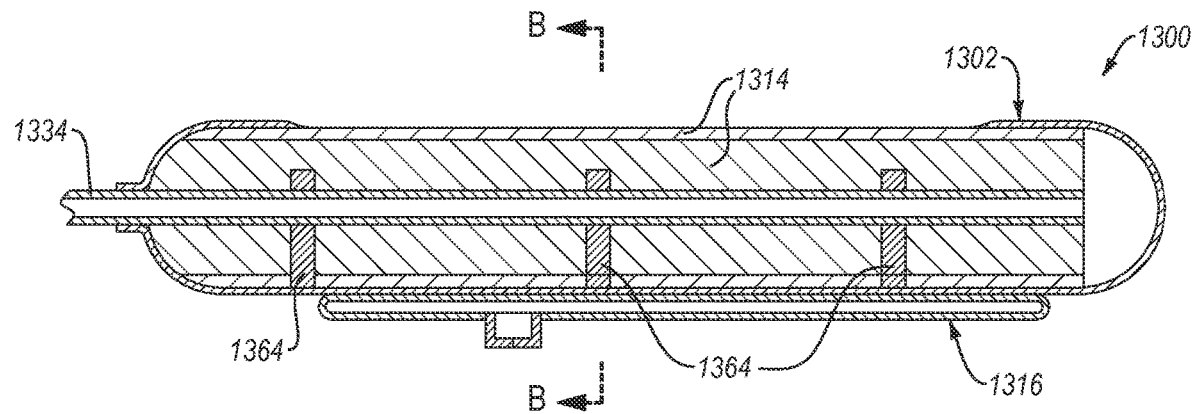
FIG. 13A is a cross-sectional view of a fluid collection assembly, according to an embodiment.
Figure 13B:
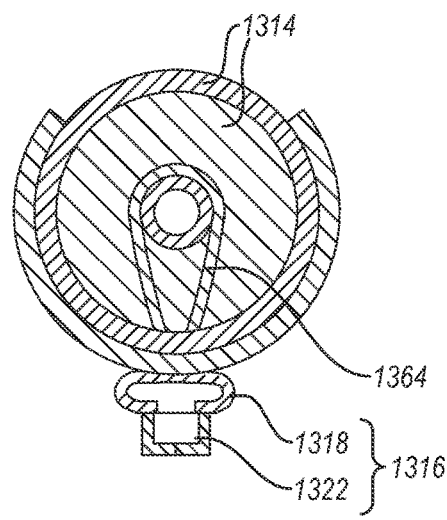
FIG. 13B is a cross-sectional view of the fluid collection assembly taken along plane B-B of FIG. 13A, according to an embodiment.

The fluid collection assemblies disclosed herein may include one or more structures that are configured to force the conduit to exhibit the desired shape change and minimize the normal force that is applied to the porous material. FIG. 13A is a cross-sectional view of a fluid collection assembly 1300, according to an embodiment. FIG. 13B is a cross-sectional view of the fluid collection assembly 1300 taken along plane B-B of FIG. 13A, according to an embodiment. Except as otherwise disclosed herein, the fluid collection assembly 1300 is the same or substantially similar at any of the fluid collection assemblies disclosed herein. For example, the fluid collection assembly 1300 includes a fluid impermeable barrier 1302, a porous material 1314, a conduit 1334, and at least one inflation device 1316. In the illustrated embodiment, the fluid collection assembly 1300 is illustrated as being substantially similar to the fluid collection assembly 100 shown in FIGS. 1A-1E. However, as previously discussed, the fluid collection assembly 1300 may be substantially similar to any of the fluid collection assemblies disclosed herein.

The fluid collection assembly 1300 includes at least one brace 1364 that is configured to force the conduit 1334 to exhibit a shape change that corresponds more closely to the shape change of the inflation device 1316 than if the fluid collection assembly 1300 did not include the brace 1364. The brace 1364 also minimizes the normal force applied from the conduit 1334 to the porous material 1314. The brace 1364 is connected to the inflation device 1316 or a component of the fluid collection assembly 1300 that is connected to the inflation device 1316 (e.g., the fluid impermeable barrier 1302 when the inflation device 1316 is attached to an exterior surface of or embedded within the fluid impermeable barrier 1302). The brace 1364 extends from the inflation device 1316 or the component of the fluid collection assembly 1300 that is connected to the inflation device 1316 to the conduit 1334. For example, the brace 1364 may extend around the conduit 1334, as shown in FIG. 13B. It is noted that the brace 1364 may be attached to the conduit 1334 using other suitable techniques, such as with an adhesive. To allow the brace 1364 to extend to the conduit 1334, one or more components of the fluid collection assembly 1300 (e.g., the porous material 1314) may include one or more slits formed therein through which the braces 1364 extend. The brace 1364 may be configured to transfer a shape change in the inflation device 1316 to the conduit 1334 such that the conduit 1334 exhibits a shape change that substantially corresponds to the shape change of the inflation device 1316.

The fluid collection assembly 1300 may include any suitable number of braces 1364, such as 1, 2, 3, 4, 5, 6, 7, 8, 9, 10, or greater than 10 braces 1364. Generally increasing the number of braces 1364 causes the conduit 1334 to more accurately correspond to the shape of the inflation device 1316 and decreases the normal force that is applied to the porous material 1314.

It is noted that the braces 1364 may not always cause the conduit 1334 to exhibit the same shape change as the inflation device 1316. For example, when the braces 1364 are looped around and are not attached to the conduit 1334 (as shown), the braces 1364 may only cause the conduit 1334 to exhibit the shape change of the inflation device 1316 when the braces 1364 pull (e.g., the braces 1364 are in tension) the conduit 1334 towards the inflation device 1316 but not when the braces 1364 push (e.g., the braces 1364 are in compression) the conduit 1334 away from the inflation device 1316.

Figure 14:
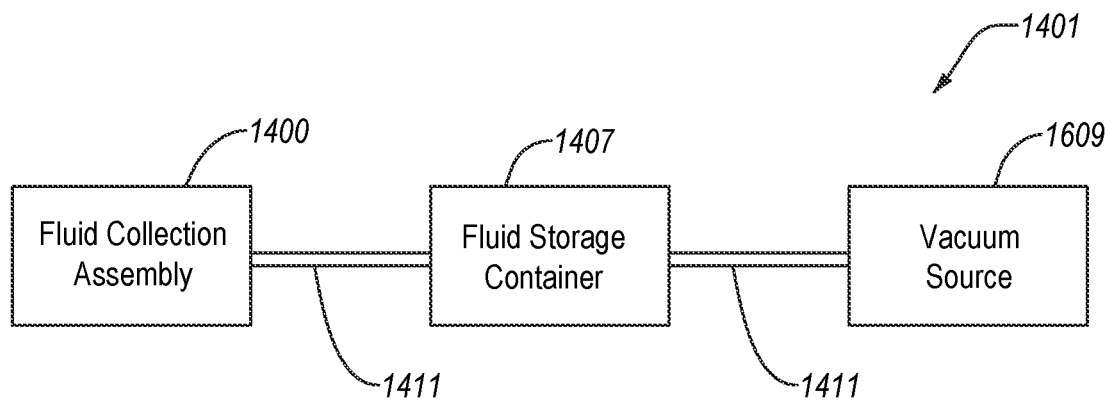
FIG. 14 is a block diagram of a system for fluid collection, according to an embodiment.

FIG. 14 is a block diagram of a system 1401 for fluid collection, according to an embodiment. The system 1401 includes a fluid collection assembly 1400, a fluid storage container 1407, and a vacuum source 1409. The fluid collection assembly 1400, the fluid storage container 1407, and the vacuum source 1409 may be fluidly coupled to each other via one or more conduits 1411. For example, fluid collection assembly 1400 may be operably coupled to one or more of the fluid storage container 1407 or the vacuum source 1409 via the conduit 1411. Fluid (e.g., urine or other bodily fluids) collected in the fluid collection assembly 1400 may be removed from the fluid collection assembly 1400 via the conduit 1411 which protrudes into the fluid collection assembly 1400. For example, an inlet of the conduit 1411 may extend into the fluid collection assembly 1400, such as to a fluid reservoir therein. The outlet of the conduit 1411 may extend into the fluid collection assembly 1400 or the vacuum source 1409. Suction force may be introduced into the chamber of the fluid collection assembly 1400 via the inlet of the conduit 1411 responsive to suction (e.g., vacuum) force applied at the outlet of the conduit 1411.

The suction force may be applied to the outlet of the conduit 1411 by the vacuum source 1409 either directly or indirectly. The suction force may be applied indirectly via the fluid storage container 1407. For example, the outlet of the conduit 1411 may be disposed within the fluid storage container 1407 and an additional conduit 1411 may extend from the fluid storage container 1407 to the vacuum source 1409. Accordingly, the vacuum source 1409 may apply suction to the fluid collection assembly 1400 via the fluid storage container 1407. The suction force may be applied directly via the vacuum source 1409. For example, the outlet of the conduit 1411 may be disposed within the vacuum source 1409. An additional conduit 1411 may extend from the vacuum source 1409 to a point outside of the fluid collection assembly 1400, such as to the fluid storage container 1407. In such examples, the vacuum source 1409 may be disposed between the fluid collection assembly 1400 and the fluid storage container 1407.

The fluid collection assembly 1400 may be similar or identical to any of the fluid collection assemblies disclosed herein in one or more aspects. The fluid collection assembly 1400 may be shaped and sized to be positioned adjacent to a female urethral opening. For example, the fluid collection assembly 1400 may include a fluid impermeable barrier at least partially defining a chamber (e.g., interior region) of the fluid collection assembly 1400. The fluid impermeable barrier also defines at least one opening extending therethrough from the external environment. The opening may be positioned adjacent to the female urethral opening. The fluid collection assembly 1400 may include porous material disposed in the chamber, such as one or more of a fluid permeable support and a fluid permeable membrane. The fluid collection assembly 1400 includes at least one inflation device on or incorporated in one or more components thereof. The inflation device include a bladder that is configured to change a shape thereof when the bladder is switched between the first and second states. The conduit 1411 may extend into the fluid collection assembly 1400 at a first end (e.g., proximal) region, through one or more of the fluid impermeable barrier or the porous material to a second end region of the fluid collection assembly 1400. The conduit 1411 includes an inlet and an outlet, the outlet being fluidly coupled to the fluid storage container and the inlet being positioned in a portion of the chamber selected to be at a gravimetrically low point of the fluid collection assembly when worn.

The fluid storage container 1407 is sized and shaped to retain a fluid therein. The fluid storage container 1407 may include a bag (e.g., drainage bag), a bottle or cup (e.g., collection jar), or any other enclosed container for storing bodily fluid(s) such as urine. In some examples, the conduit 1411 may extend from the fluid collection assembly 1400 and attach to the fluid storage container 1407 at a first point therein. An additional conduit 1411 may attach to the fluid storage container 1407 at a second point thereon and may extend and attach to the vacuum source 1409. Accordingly, a vacuum (e.g., suction) may be drawn through fluid collection assembly 1400 via the fluid storage container 1407. Fluid, such as urine, may be drained from the fluid collection assembly 1400 using the vacuum source 1409.

The vacuum source 1409 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 1409 may provide a vacuum or suction to remove fluid from the fluid collection assembly 1400. In some examples, the vacuum source 1409 may be powered by one or more of a power cord (e.g., connected to a power socket), one or more batteries, or even manual power (e.g., a hand operated vacuum pump). In some examples, the vacuum source 1409 may be sized and shaped to fit outside of, on, or within the fluid collection assembly 1400. For example, the vacuum source 1409 may include one or more miniaturized pumps or one or more micro pumps. The vacuum sources 1409 disclosed herein may include one or more of a switch, a button, a plug, a remote, or any other device suitable to activate the vacuum source 1409.

Figure 15:
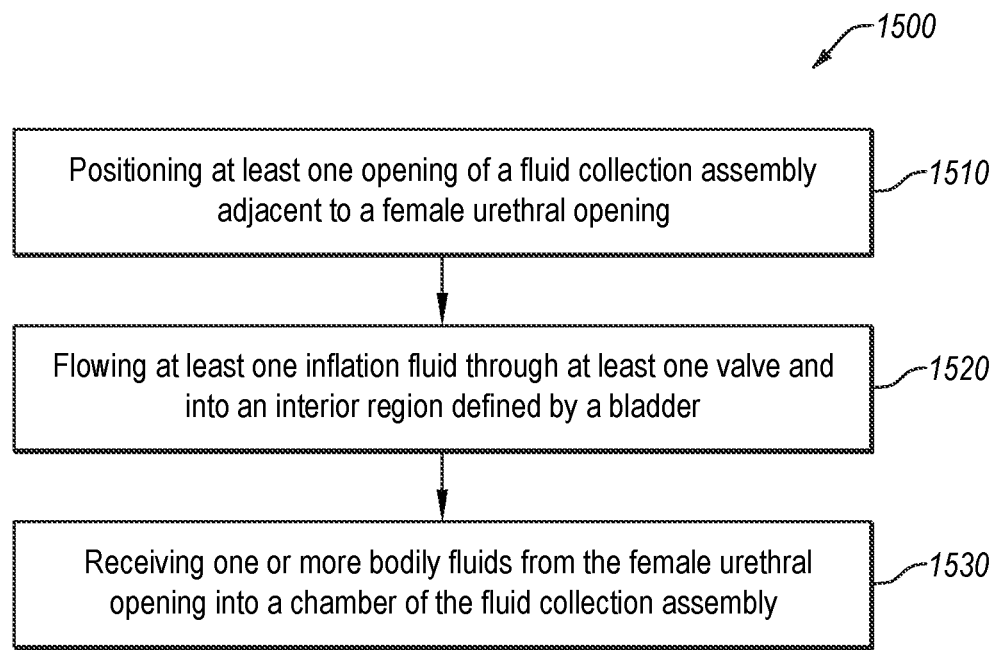
FIG. 15 is a flow diagram of a method to collect fluid, according to an embodiment.

FIG. 15 is a flow diagram of a method 1500 to collect fluid, according to an embodiment. The method 1500 of collecting fluid may utilize use any of the fluid collection assemblies and/or fluid collection systems disclosed herein. The method 1500 may include act 1510, which recites "positioning at least one opening of a fluid collection assembly adjacent to a female urethral opening." Act 1510 may be followed by act 1520, which recites "flowing at least one inflation fluid through at least one valve and into an interior region defined by a bladder." Act 1520 may be followed by act 1530, which recites "receiving one or more bodily fluids from the female urethral opening into a chamber of the fluid collection assembly."

Acts 1510, 1520, 1530 of the method 1500 are for illustrative purposes. For example, the act 1510, 1520, 1530 of the method 1500 may be performed in different orders, split into multiple acts, modified, supplemented, or combined. In an example, one or more of the acts 1510, 1520, 1530 of the method 1500 may be omitted from the method 1500. Any of the acts 1510, 1520, or 1530 may include using any of the fluid collection assemblies or systems disclosed herein.

Act 1510 recites "positioning at least one opening of a fluid collection assembly adjacent to a female urethral opening." The act 1510 of positioning the opening of a fluid collection assembly adjacent to a female urethral opening may include utilizing any of the fluid collection assemblies or systems disclosed herein. In some examples, act 1510 may include positioning the opening of a fluid collection assembly such that the fluid permeable membrane of the female fluid collection assembly abuts or is positioned proximate to the female urethral opening. In some examples, positioning an opening of a fluid collection assembly adjacent to a female urethral opening may include positioning the opening over the female urethral opening, such as positioning a longitudinally extending opening of the fluid collection assembly over the female urethral opening.

Act 1520 recites "flowing at least one inflation fluid through at least one valve and into an interior region defined by a bladder." Flowing the inflation fluid into the interior region may switch the bladder between a first state and at least a second state which, in turn, shapes the bladder and at least a portion of the rest of the fluid collection assembly between a first (e.g., initial) shape and a second shape. For example, switching the bladder from the first state to the second state may include shaping a female fluid collection assembly to contour to the anatomy around the urethral opening. In some embodiments, switching the bladder from the first state to the second state may include forming the (e.g., a longitudinal shape of the) fluid collection assembly into an arcuate shape conforming to the perineal region of the patient. For example, switching the bladder from the first state to the second state may include forming the fluid collection assembly into an arcuate shape conforming to the vaginal and perineal region of a patient.

Act 1530 recites, "receiving one or more bodily fluids from the female urethral opening into a chamber of the fluid collection assembly." In some examples, receiving bodily fluids from the female urethral opening into a chamber of the fluid collection assembly includes receiving the bodily fluids through the opening of the fluid collection assembly. Receiving bodily fluids from the female urethral opening into a chamber of the fluid collection assembly may include wicking the bodily fluids away from the opening using porous material, such as via a fluid permeable membrane and a fluid permeable support. Receiving bodily fluids from the female urethral opening into a chamber of the fluid collection assembly may include flowing the bodily fluids towards a portion of the chamber that is fluidly coupled to an inlet of a conduit in fluid communication a vacuum source. For instance, receiving bodily fluids from the female urethral opening into a chamber of the fluid collection assembly may include flowing the bodily fluids to a substantially unoccupied portion of the chamber (e.g., a fluid reservoir), to a gravimetrically low point of the chamber, etc., such as via gravity, wicking, or suction force. In some examples, wicking the bodily fluids into the chamber via the fluid permeable membrane and fluid permeable support may include wicking urine into a fluid reservoir in the fluid collection assembly.

The method 1500 may include applying suction with a vacuum source effective to suction the bodily fluids from the chamber via a conduit disposed therein and fluidly coupled to the vacuum source may include using any of the vacuum sources disclosed herein. Applying suction with a vacuum source may include activating the vacuum source (e.g., suction device) in fluid communication with the inlet of the conduit in the fluid collection assembly. In some examples, activating the vacuum source in fluid communication with the inlet of the conduit in the fluid collection assembly may include supplying power to the vacuum source by one or more of flipping an on/off switch, pressing a button, plugging the vacuum source into a power outlet, putting batteries into the vacuum source, etc. In some examples, the vacuum source may include a hand operated vacuum pump and applying suction with a vacuum source may include manually operating the hand operated vacuum pump effective to suction the bodily fluids from the chamber via the conduit disposed therein that is fluidly coupled to the vacuum source.

In some examples, applying suction with a vacuum source effective to suction the bodily fluids from the chamber via a conduit disposed therein and fluidly coupled to the vacuum source may be effective to remove at least some bodily fluids (e.g., urine) from the chamber (e.g., interior region) of the fluid collection assembly. In some examples, applying suction with a vacuum source effective to suction the bodily fluids from the chamber via a conduit disposed therein and fluidly coupled to the vacuum source may be effective to transfer at least some of the bodily fluids from the chamber to a fluid storage container (e.g., a bottle or bag), such as from one or more of a reservoir, fluid permeable support, or fluid permeable membrane.

In some examples, the vacuum source (e.g., suction device) may be disposed on or within the fluid collection assembly and applying suction with the vacuum source may include activating the vacuum source. In some examples, the vacuum source may be spaced from the fluid collection assembly and applying suction with the vacuum source may include activating the vacuum source.

In some examples, applying suction with a vacuum source effective to suction the bodily fluids from the chamber via a conduit disposed therein and fluidly coupled to the vacuum source may include detecting moisture in the chamber (e.g., via one or more moisture sensors) and responsive thereto, activating the vacuum source to provide suction in the chamber. The control of the vacuum source responsive to the signals indicating that moisture or a level thereof is present in the chamber may be automatic, such as via a controller (e.g., computer programmed to perform the operation), or may merely provide an indication that a level of moisture is present that may necessitate removal of fluid from the chamber of the fluid collection assembly. In the latter case, a wearer may receive the indication (e.g., from the controller) and activate the vacuum pump manually.

In an example, the method 1500 may include collecting the bodily fluids that are removed from the fluid collection assembly, such as into a fluid storage container that is spaced from the fluid collection assembly and fluidly coupled to the conduit. The fluid storage container may include any of the fluid storage containers disclosed herein.

The fluid collection assemblies disclosed herein are configured to collect one or more bodily fluids from a female urethral opening. However, it is noted that any of the concepts disclosed herein, such as inflation devices, may be configured to collect one or more bodily fluids from a male urethral opening (e.g., penis). Examples of fluid collection assemblies that are configured to collected bodily fluids from a male urethral opening and methods of using such fluid collection assemblies are disclosed in International Application No. PCT/US20/42262 filed on Jul. 14, 2020, U.S. patent application Ser. No. 14/433,773 filed on Apr. 3, 2020, and U.S. Provisional Patent Application No. 63/047, 374 filed on Jul. 2, 2020, the disclosure of each of which is incorporated herein, in its entirety, by this reference.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. In an example, when the term of degree is included with a term indicating quantity, the term of degree is interpreted to mean±10%, ±5%, or ±2% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

We claim:

1. A fluid collection assembly, comprising:
a fluid impermeable barrier defining a chamber, at least one opening, and at least one fluid outlet, the fluid impermeable barrier including at least one proximal surface defining the at least one opening and at least one distal surface opposite the proximal surface;
at least one porous material disposed in the chamber; and
at least one inflation device including:
a bladder positioned external the chamber and coupled to the at least one distal surface of the fluid impermeable barrier, the bladder including one or more walls defining at least one interior region, the bladder configured to switch between a first state and at least a second state, wherein a volume of the at least one interior region is greater when the bladder is in the second state than when the bladder is in the first state; and
at least one valve configured to selectively permit at least one inflation fluid to flow into and out of the at least one interior region to switch the bladder between the first state and at least the second state, the at least one valve including a two-way valve;
wherein switching the bladder between the first state and the second state changes a curvature of at least a portion of the fluid impermeable barrier.

2. The fluid collection assembly of claim 1, wherein the at least one inflation device includes a first region adjacent to the at least one distal surface of the fluid impermeable barrier and a second region opposite the first region, and wherein an expansion rate of the first region is less than an expansion rate of the second region.

3. The fluid collection assembly of claim 2, wherein the at least one inflation device includes at least one additional layer attached to at least a portion of the first region.

4. The fluid collection assembly of claim 3, wherein the at least one additional layer includes a substantially inflexible fabric.

5. The fluid collection assembly of claim 3, wherein the at least one additional layer includes a wire, plate, a substantially inflexible polymer, metal, or composite.

6. The fluid collection assembly of claim 2, wherein at least a portion of the first region exhibits a thickness that is greater than an opposing portion of the second region.

7. The fluid collection assembly of claim 2, wherein at least a portion of the first region is directly attached to the fluid impermeable barrier.

8. The fluid collection assembly of claim 7, wherein the at least a portion of the first region is directly attached to the corresponding portion of the at least one distal surface.

9. The fluid collection assembly of claim 1, wherein the at least one inflation device includes a crinkle shaped bladder.

10. The fluid collection assembly of claim 1, wherein the fluid impermeable barrier includes at least one lateral surface extending between the at least one proximal surface and the at least one distal surface, and wherein the at least one inflation device is not adjacent to the at least one lateral surface or the at least one proximal surface.

11. The fluid collection assembly of claim 1, wherein the at least one inflation device includes a plurality of inflation devices adjacent to the at least one distal surface.

12. The fluid collection assembly of claim 11, wherein each of the plurality of inflation devices are configured to control the curvature of different portions of the rest of the fluid collection assembly.

13. The fluid collection assembly of claim 1, wherein the at least one valve includes a plurality of valves, at least one of the plurality of valves includes a one-way valve.

14. The fluid collection assembly of claim 1, wherein the bladder is configured to substantially prevent a change in a volume of the at least one porous material when the bladder switches between the first and second states.

15. The fluid collection assembly of claim 1, wherein the two-way valve includes at least one of a luer valve or a fluid impermeable membrane with a slit or opening formed therein.

16. A system, comprising:
a fluid collection assembly including:
   a fluid impermeable barrier defining a chamber, at least one opening, and at least one fluid outlet, the fluid impermeable barrier including at least one proximal surface defining the at least one opening and at least one distal surface opposite the proximal surface;
   at least one porous material disposed in the chamber; and
   at least one inflation device including:
      a bladder positioned external the chamber and coupled to the at least one distal surface of the fluid impermeable barrier, the bladder including one or more walls defining at least one interior region, the bladder configured to switch between a first state and at least a second state, wherein a volume of the at least one interior region is greater when the bladder is in the second state than when the bladder is in the first state; and
      at least one valve configured to selectively permit at least one inflation fluid to flow into and out of the at least one interior region to switch the bladder between the first state and at least the second state, the at least one valve including a two-way valve:
      wherein switching the bladder between the first state and the second state changes a curvature of at least a portion of the fluid impermeable barrier;
a fluid storage container; and
a vacuum source;
wherein the chamber of the fluid collection assembly, the fluid storage container, and the vacuum source are in fluid communication with each other via one or more conduits.

17. The system of claim 16, further comprising at least one pump in fluid communication with the at least one valve, the at least one pump configured to provide at least one inflation fluid to switch the bladder from the first state to the second state.

18. The system of claim 17, further comprising one or more sensors configured to detect contact between the fluid collection assembly and an patient, the one or more sensors communicably coupled to a control electric circuitry, the control electric circuitry configured to control the pump responsive to receiving one or more signal from the one or more sensors.

19. A method of using a fluid collection assembly, the method comprising:
   positioning at least one opening of the fluid collection assembly adjacent to a female urethral opening, the fluid collection assembly including:
      a fluid impermeable barrier defining a chamber, the at least one opening, and at least one fluid outlet, the fluid impermeable barrier including at least one proximal surface defining the at least one opening and at least one distal surface opposite the proximal surface;
      at least one porous material disposed in the chamber; and
      at least one inflation device including a bladder positioned external to the chamber and coupled to the at least one distal surface of the fluid impermeable barrier, the bladder including one or more walls defining at least one interior region, the bladder configured to switch between a first state and at least a second state and at least one valve configured to selectively permit at least one inflation fluid to flow into and out of the at least one interior region to switch the bladder between the first state and at least the second state, the at least one valve including a two-way valve; and
   flowing at least one inflation fluid through the at least one valve and into the at least one interior region of the at least one inflation device to change a curvature of the fluid impermeably barrier.

20. The method of claim 19, wherein the at least one inflation fluid includes at least one gas.

* * * * *